US006177472B1

(12) United States Patent
Wilson et al.

(10) Patent No.: US 6,177,472 B1
(45) Date of Patent: Jan. 23, 2001

(54) REGULATION OF ALZHEIMER'S DISEASE PROTEINS AND USES THEREOF

(75) Inventors: David M. Wilson, West Roxbury, MA (US); Lester I. Binder, Graystake, IL (US)

(73) Assignee: University of Alabama at Birmingham Research Foundation, Birmingham, AL (US)

(*) Notice: Under 35 U.S.C. 154(b), the term of this patent shall be extended for 0 days.

(21) Appl. No.: 09/179,777

(22) Filed: Oct. 27, 1998

Related U.S. Application Data

(63) Continuation of application No. 08/689,395, filed as application No. PCT/US96/12905 on Aug. 7, 1996, now abandoned.
(60) Provisional application No. 60/602,023, filed on Aug. 8, 1995.

(51) Int. Cl.[7] .................. A61K 31/135; A61K 31/05; A61K 31/12; A61K 31/125
(52) U.S. Cl. .................. 514/646; 514/731; 514/688; 514/692
(58) Field of Search .................. 514/646, 731, 514/688, 692

(56) References Cited

U.S. PATENT DOCUMENTS 4,946,857 * 8/1990 Kanehira et al. .................. 514/399

OTHER PUBLICATIONS

Shankle, W.R. et al., "Low–Dose . . . Elderly Demented Patients"; Alzheimer Disease and Associated Disorders; vol. 9, pp. 233–237. (1995).*

Decker, M.W. et al., "Concurrent muscarinic and .beta.–adrenergic blocade in rats impaiirs place–learning in a water maze and retention of inhibitory avoidance"; Brain Res., vol. 513, pp. 81–85, 1990.*

Wilson et al., "In vitro polymerization of microtubule–associate protein tau and amyloid peptide A4 1–40 is stimulated by free fatty acids", Molecular Biology of the Cell, p. 37A, Abstract 218, vol. 6, Issued 1995.

Kinouchi et al., "Arachidonate metabolites affect the secretion of an N–terminal fragment of Alzheimer's Disease amyloid precursor protein", Biochemical and Biophysical Research Communications, vol. 209, No. 3, issued 1995, pp. 841–849.

Goux et al., "Analysis of the core components of Alzheimer paired helical filaments. A gas chromatography/mass spectrometry characterization of fatty–acids carbohydrates and long–chain bases", FEBS Letters, vol. 366, No. 1, issued Jun. 5, 1995, pp. 81–85.

Leon et al., "Development and survival of neurons in dissociated mesencephalic serum–free cell cultures. II. Modulatory effects of ganliosides", Journal of Neuroscience vol. 8, No. 3, issued Mar., 1988, pp. 746–753.

Gordon, G. B., "Saturated free fatty acid toxicity. II. Lipid accumulation, ultrastructural alterations, and toxicity in mammalian cells in culture", vol. 27, No. 2, Issued Oct. 19, 1977, pp. 262–276.

* cited by examiner

Primary Examiner—Theodore J. Criares
(74) Attorney, Agent, or Firm—Fitch, Even, Tabin & Flannery

(57) ABSTRACT

A method of regulating the assembly of the protein tau in the brain of a mammal in need of such treatment comprising the step of administering to said mammal a pharmacologically effective amount of a fatty acid liberation or release inhibitor. Also provided is a method of inhibiting production of Alzheimer-type amyloidosis in a mammal comprising the step of administering to said mammal in need of such treatment an effective amount of at least one modulator of fatty acid liberation or release, said modulator capable of controlling the rate of assembly of proteins found in intracellular neurofibrillary tangles and extracellular amyloid plaques. In another embodiment of the present invention, there is provided a method of stimulating polymerization of a tau protein, comprising the step of contacting said protein with a fatty acid. In another embodiment of the present invention, there is provided a method of stimulating polymerization of a amyloid peptide, comprising the step of contacting said peptide with a fatty acid.

5 Claims, 17 Drawing Sheets

Effects of Different Fatty Acids on Tau Polymerization

| Fatty Acid<br>(50 μM, all cis) | Polymer Mass<br>(μm/field) | % max<br>(20:4) | CMC<br>(mM) |
|---|---|---|---|
| control (no fatty acid) | 0.63 | 3 | NA |
| 5,8,11,14,17-eicosapentaenoic acid (20:5) | 11.81 | 48 | 0.16 |
| 5,8,11,14-eicosatetraenoic acid (20:4) | 24.51 | 100 | NA |
| 8,11,14-eicosatrienoic acid (20:3) | 7.99 | 33 | NA |
| 11,14-eicosadienoic acid (20:2) | 1.20 | 5 | NA |
| 11-eicosanoic acid (20:1) | 8.23 | 34 | NA |
| eicosanoic acid (20:0) | 0.77 | 3 | NA |
| 9,12,15-linolenic acid (18:3) | 4.01 | 16 | 0.21 |
| 9,12-linoleic acid (18:2) | 14.74 | 60 | 0.59 |
| 9-oleic acid (18:1) | 7.36 | 30 | >1 |
| stearic acid (18:0) | 3.60 | 15 | 0.44 |
| 9-palmitoleic acid (16:1) | 23.69 | 97 | NA |
| palmitic acid (16:0) | 7.37 | 30 | NA |
| myristic acid (14:0) | 5.50 | 22 | >1 |

Figure 12

REGULATION OF ALZHEIMER'S DISEASE PROTEINS AND USES THEREOF

This is a continuation, of prior application Ser. No. 08/689,395, filed Jun. 13, 1997, now abandoned which is based on PCT Application No. PCT/US96/12905, filed Aug. 7, 1996, which is based on U.S. Provisional Application No. 60/602,023, filed Aug. 8, 1995, which is hereby incorporated herein by reference in its entirety.

FEDERAL FUNDING LEGEND

This invention was funded in part by NIH grants AG09031 and AG06569. The federal government has, therefore certain rights in this invention.

BACKGROUND OF THE INVENTION

1. Field of the Invention

The present invention relates generally to the fields of neurology and protein chemistry. More specifically, the present invention relates to the regulation of Alzheimer's disease related proteins and uses thereof.

2. Description of the Related Art

Alzheimer's disease is a brain disorder characterized by altered protein catabolism. From the work of several laboratories, altered protein deposition has been implicated in the formation of intracellular neurofibrillary tangles found in Alzheimer's disease. The intracellular fibrillar pathology of Alzheimer's disease is characterized by the presence of filaments having a straight or paired helical morphology (Kidd, 1963; Yagishita et al., 1981). These filaments accumulate in both the somal neurofibrillary tangles (neurofibrillary tangle)l and the dystrophic neuropil threads (Braak et al, 1986; Kowall and Kosik, 1987). The formation of neurofibrillary tangle and dystrophic neurites are spatially correlated (Probst et al., 1989; Yamaguchi et al., 1990), and both lesions are highly correlated with the severity of dementia (McKee et al., 1991). Filamentous inclusions of this type are also seen in Down's syndrome (Wisniewski et al., 1985), Guamanian Parkinsonism-dementia (Hirano et al., 1968), and other disease states (Wisniewski et al., 1979). In progressive supranuclear palsy, neurofibrillary tangle are composed primarily of filaments possessing the straight, unpaired morphology (Tellez-Nagel and Wisniewski, 1973; Bugiani et al., 1979). Though the death of polymer-laden neurons is evidenced by the presence of insoluble tangle remnants in the extracellular space, it is not known whether polymer masses disrupt neuronal function sufficiently to induce degeneration, or whether they merely form preferentially within neurons already involved in the necrotic process.

Straight filaments (SF) and paired helical filaments (paired helical filament) form under similar conditions, as evidenced by their co-existence within individual neurofibrillary tangle (Perry et al., 1987). Straight filaments share epitopes with paired helical filaments and copurify with paired helical filaments in protocols which exploit their resistance to SDS or protease treatments (Perry et al., 1987; Crowther, 1991). In addition, there are several reports of transitional forms of fibrils possessing stretches of straight then paired helical morphology continuous within a single filament (Wischik et al., 1985; Perry et al., 1987; Papasozomenos, 1989; Crowther, 1991). These findings and others have led to speculation that straight filaments and paired helical filaments are formed by similar mechanisms of assembly (Perry et al., 1987; Crowther, 1991; Wille et al., 1992).

The only known structural constituent of the paired helical filaments is the microtubule-associated protein tau (for a review of the normal biology of tau; see Lee, 1990). The presence of tau proteins has been demonstrated by both immunochemical means (Grundke-Iqbal et al., 1986; Kosik et al., 1986), and by sequencing of peptides extracted from paired helical filaments (Wischik et al., 1988; Kondo et al., 1988). Tau extracted from paired helical filaments contains more phosphorylated residues than tau isolated from normal brain (Hasegawa et al., 1992; Ksiezak-Reding et al., 1992), and these phosphorylations are frequently invoked as being involved in the polymerization process.

Tau purified directly from brain or from brain microtubules (MT) has been reported to form a variety of polymers resembling straight filaments or paired helical filaments. Dialysis of porcine microtubule tau for several days against 6–8 M urea produced polymers ranging in width from 5–35 nm, which included a subset resembling paired helical filaments (Montejo de Garcini et al., 1986; Montejo de Garcini and Avila, 1987). The effects of urea were attributed to deamination of glutamine residues or carbamylation of lysine residues, although producing these modifications by enzymatic or chemical means did not fully reproduce the effects of urea treatment alone. Urea treated tau was reported to assemble independent of NaCl concentration in the range of 0.1–1M. Using tau purified directly from bovine whole brain, 10 nm filaments were formed in the presence of the cross-linking enzyme, transglutaminase, under conditions optimized for enzymatic activity (Dudek and Johnson, 1993). It is unlikely that this enzyme is required for tau polymerization in vivo, however, since monomeric tau is solubilized from isolated neurofibrillary tangle (Greenberg and Davies, 1990; Lee et al., 1991). Polymer formation has also been demonstrated using bacterially expressed human recombinant tau. Two groups using deletion constructs roughly equivalent to the microtubule binding domain of tau and similar acidic conditions produced several polymer species which included a subset possessing the twisted morphology of paired helical filaments (Wille et al., 1992; Crowther et al., 1992). Full length tau constructs did not assemble under these conditions. More recently, however, using conditions of neutral pH and high ionic strength (1.25 M $CH_3CO_2$-$K^+$), full length tau constructs were observed to form filaments, some of which resembled paired helical filaments (Crowther et al., 1994).

The establishment of causal relationships between the assembly of tau into straight filaments and paired helical filaments, and potential modulating factors such as phosphorylation or other enzymatic or chemical treatments, would benefit from an in vitro assembly system in which these polymers can be demonstrated to form under physiologically relevant conditions. Although kinetically a relatively slow process, in vitro filament formation is observed under essentially physiological conditions.

The prior art is deficient in the lack of effective means of determining the conditions in which tau purified from rat or porcine microtubule will assemble into a homogenous population of filaments resembling straight filaments and regulating the proliferation of tau. The present invention fulfills this longstanding need and desire in the art.

SUMMARY OF THE INVENTION

In one embodiment of the present invention, there is provided a method of regulating the assembly of the protein tau in the brain of a mammal in need of such treatment comprising the step of administering to said mammal a pharmacologically effective amount of a fatty acid liberation or release inhibitor.

In another embodiment of the present invention, there is provided a method of inhibiting production of Alzheimer-type amyloidosis in a mammal comprising the step of administering to said mammal in need of such treatment an effective amount of at least one modulator of fatty acid liberation or release, said modulator capable of controlling the rate of assembly of proteins found in intracellular neurofibrillary tangles and extracellular amyloid plaques.

In still yet another embodiment of the present invention, there is provided a method of treating amyloidosis associated with Alzheimer's disease in a mammalian patient comprising the step of administering to said patient in need of such treatment an effective amount of at least one modulator of fatty acid liberation or release, said modulator capable of controlling the rate of assembly of proteins found in intracellular neurofibrillary tangles and extracellular amyloid plaques.

In another embodiment of the present invention, there is provided a method of stimulating polymerization of a tau protein, comprising the step of contacting said protein with a unesterified fatty acids.

In another embodiment of the present invention, there is provided a method of stimulating polymerization of a amyloid peptide, comprising the step of contacting said peptide with a fatty acid.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

(FIGS. 5A–E) or 37° C. (FIGS. 5F–J) for 15 minutes (FIGS. 5A, 5F), 30 minutes (FIGS. 5B, 5G), 60 minutes (FIGS. 5C, 5H), 120 minutes (FIGS. 5D, 5I), or 240 minutes (FIGS. 5E, 5J). Samples were processed for EM and representative fields were recorded. Bar equals 1.5 microns.

(FIGS. 6A–6E) or 37° C. (FIGS. 6F–6J) for the indicated number of hours (t). Histograms were generated using filament measurements obtained as described below. Average filament length (x) and sample size (n) are also given for each data set. Bin width is 200 nm.

FIGS. 9A–E. Porcine microtubule tau was incubated 24 hours. with the indicated concentration of DTT. Samples were deposited on grids and filaments from 10 randomly chosen fields were digitized and measured. Bin width is 300 nm. FIG. 9F shows that the average length of each filament population is plotted as a function of DTT concentration.

FIG. 10A: Samples of juvenile rat MTt used at 100 (~2.5 μM) were supplemented with the indicated concentrations of arachidonic acid and assembled for 24 hours (filled squares), 66 hours (open squares), 108 hours (filled circles), or 214 hours (open circles). FIG. 10B shows the data from FIG. 10A, with polymer mass replotted as a function of time. Samples were incubated in the presence of 20 µM (filled circles), 40 µM (open circles), or 80 µM arachidonic acid (filled squares). FIG. 10C shows the Tau polymers were assembled from adult rat MTt (100 mg/ml) (filled circles), tau purified from porcine whole brain (200 µg/ml) (open circles), or purified human recombinant tau expressed in *E. coli* (200 µg/ml) (filled squares). Samples were incubated 66 hours. General conclusions cannot be made regarding the relative efficacy of assembly of tau purified by the different methods, due to the different species of origin. All samples (FIG. 10A and FIG. 10B) were negative stained with 2% uranyl acetate and electron micrographs of random fields were digitized and traced. Values shown are the average summed polymer length/field ±S.E.M., n≧12.

FIG. 13A shows the samples of juvenile (open circles) or adult tau (filled squares) were incubated at 4° C., 22° C., or 37° C. (FIG. 13B) Adult tau was assembled in the presence of the indicated concentration of NaCl (see below for the buffer conditions). FIG. 13C: adult tau was assembled in the presence of the indicated concentration of DTT. An increase in mean filament length (open circles) seen with increasing concentrations of DTT was reflected by a decrease in the number of filaments/field (filled squares).

FIGS. 14A and B shows filamentous aggregates present in solutions of amyloid peptide prior to (FIG. 14A) or following (FIG. 14B) a 24 hours incubation in the absence of free fatty acids. FIG. 14C and FIG. 14D shows long filaments resulting from a 24 hour incubation with 40 mM oleic acid (FIG. 13C) or 50 mM linoleic acid (FIG. 14D). All samples were stained with 4% uranyl acetate and photographed at a nominal magnification of 30k. Bar=275 nm.

FIG. 12 shows the effects of different fatty acids on tau polymerization. Tau polymers were assembled and quantified as described above, using tau purified from P11 rat brain microtubules. Samples were incubated for 72 hours in the presence of 50 µM fatty acid. In general, for any given chain length, unsaturated fatty acids stimulated tau assembly to a greater extent than saturated fatty acids. A 20–30 fold increase in polymer formation was observed when using arachidonic, palmitoleic, or linoleic acid. Measurements of the critical micellar concentration (CMC) of representative fatty acids under assembly conditions indicate that micellation did not contribute to, nor diminish, their stimulatory activity. CMC values were obtained based on the phase partitioning of the fluorescence indicator phenylnaphthylamine (Kovatchev, et al., (1981) *J. Biol. Chem.* 256(20): 10369–10374)

DETAILED DESCRIPTION OF THE INVENTION

Figure 1:
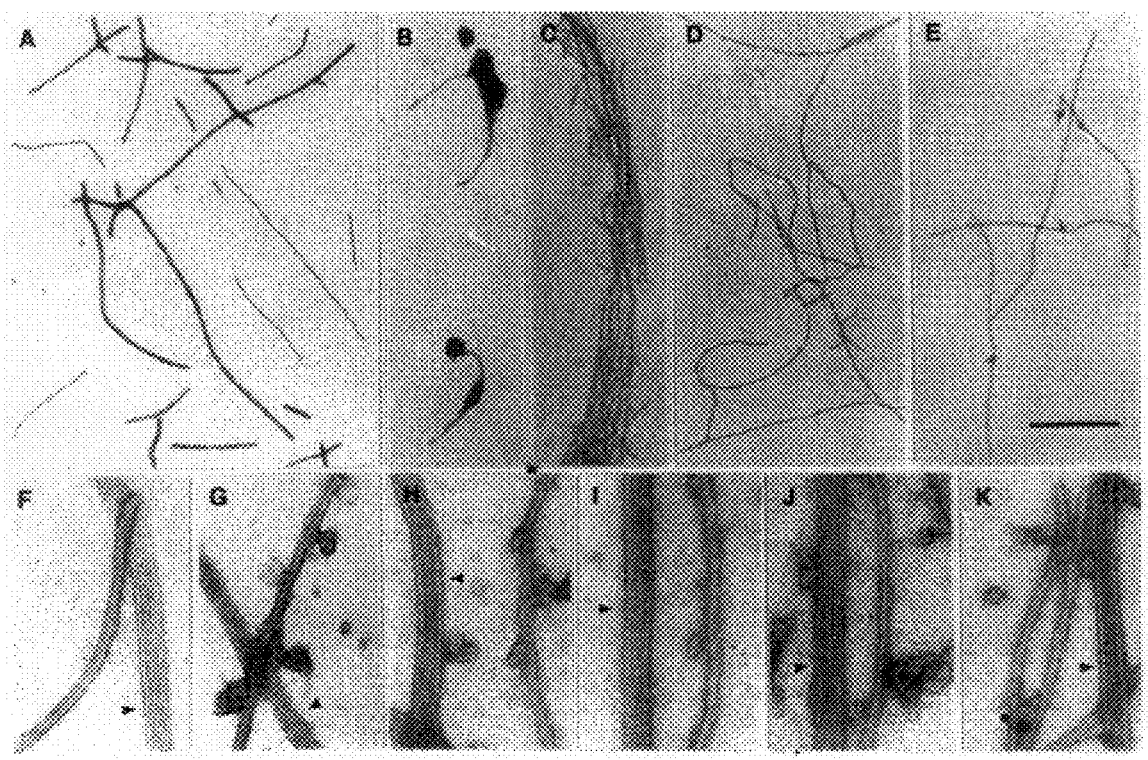
FIG. 1 shows the polymerization of rat and porcine tau protein. microtubule tau from P14 rat (FIG. 1A, FIG. 1F, FIG. 1G), P10 rat (FIG. 1B), adult rat (FIG. 1C, FIG. 1D) or adult pig (FIG. 1E, FIGS. 1H–K) was polymerized as described below and stained with uranyl acetate. In addition to dispersed preparations, typical patterns of non-filamentous (FIG. 1B) and inter-filamentous (FIG. 1C) aggregation are shown. Taxol stabilized microtubule (arrowheads) were co-precipitated on some grids for size reference. Bar equals 500 nm (FIGS. 1A–E) or 100 nm (FIGS. 1F–K).

The present invention is directed to a method of regulating the assembly of the protein tau in the brain of a mammal in need of such treatment comprising the step of administering to said mammal a pharmacologically effective amount of an inhibitor of fatty acid liberation or release. Representative examples of such fatty acids include those fatty acids listed in FIG. 12 Representative examples of such fatty acids liberation or release inhibitors include at least two types of drugs. Both of these drugs are inhibitors of lecithin cholesterol acyl transferase (LCAT). In addition to being present in the cerebrospinal fluid (CSF), this enzyme is also present in the serum, and most of the available data on inhibition of this enzyme are based on assays of serum activity. Since serum concentrations of LCAT, lipids, and cholesterol are much higher than those observed in the CSF (100- IOOOX), however, drug concentrations required for serum effects may be much higher than those required for CSF effects. The first drug is propranolol. Dosage would be in the range of 2.5–250 mg/day. This drug besides inhibiting LCAF, also inhibits lysosomal phosholipases, which are potentially involved in the intra-lysosomal nucleation of amyloid filaments. Because d-propranolol and I-propranolol have somewhat different pharmacological properties, one might want to use them separately. The second type of drug belong to the general class of terpenes, and include menthol, menthone, and camphor. Dosage for therapeutic purposes would be in concentration range of 0.2–20 mg/kg.

The present invention is also directed to a method of inhibiting production of Alzheimer-type amyloidosis in a mammal comprising the step of administering to said mammal in need of such treatment an effective amount of at least one modulator of fatty acid liberation or release, said modulator capable of controlling the rate of assembly of proteins found in extracellular amyloid plaques. Representative examples of such fatty acids liberation or release inhibitors are described above.

The present invention is also directed to a method of treating amyloidosis associated with Alzheimer's disease in a mammalian patient comprising the step of administering to said patient in need of such treatment an effective amount of at least one modulator of fatty acid liberation or release, said modulator capable of controlling the rate of assembly of proteins found in intracellular neurofibrillary tangles and extracellular amyloid plaques.

The present invention also provides a method of stimulating polymerization of a tau protein, comprising the step of contacting said protein with an unesterified fatty acids. Representative fatty acids include those listed in FIG. 12 and include arachadonic acid, palmitoleic acid, oleic acid, linoleic acid and stearic acid. This method can also be used to screen for compounds which prevent tau polymer formation in the brains of patients with AD and other related neurodegenerative diseases characterized in part by in vivo tau polymer formation.

The present invention also provides a method of stimulating polymerization of a amyloid peptide, comprising the step of contacting said peptide with a fatty acid. Representative examples of such fatty acids include arachadonic acid, palmitoleic acid, oleic acid, linoleic acid and stearic acid.

The present invention also provides a method of stimulating the polymerization of the tau polymer, comprising the step of contacting the tau polymer with a reducing agent. Representative reducing agents include dithiothreitol, dithioerythreitol, 2-mercaptothanol and reduced gluthathione. This method can be used in a screening assay to discover drugs which prevent tau polymer formation in the brains of AD patients or patients with a neurodegenerative disease characterized at least in part by increased tau polymer formation in vivo.

In another embodiment of the present invention, there is provided a method of reducing the polymerization of amyloid and/or tau proteins in the brain of an animal in need of such treatment, comprising the step of introducing into the cerebrospinal fluid of the animal, an amount of a compound effective in absorbing unesterified fatty acids in the cerebrospinal fluid.

It is specifically contemplated that pharmaceutical compositions may be prepared using the novel fatty acid liberation or release inhibitors in the methods of the present invention. In such a case, the pharmaceutical composition comprises the novel fatty acid liberation or release inhibitors and a pharmaceutically acceptable carrier. A person having ordinary skill in this art would readily be able to determine, without undue experimentation, the appropriate dosages and routes of administration of such novel fatty acid liberation or release inhibitors in the methods of the present invention.

A method of screening for a drug useful in the treatment of Alzheimer's Disease, comprising the steps of: increasing the polymerization of Aβ peptides in a medium by contacting said culture with an effective amount of at least one unesterified fatty acid or a compound that induces fatty acid liberation and release; and testing a drug of interest to determine whether the drug inhibits the polymerization of Aβ peptides induced by the unesterified fatty acid. Representative examples of useful fatty acids include arachadonic acid, palmitoleic acid, oleic acid, linoleic acid and stearic acid. Preferably, the unesterified fatty acid is found in an amount from about 1 micromolar to about 100 micromolar. A represenative example of a compound that induces fatty acid liberation and release is melittin. Preferably, the melittin is found in amount of from about 0.1 micromolar to about 1.0 micromolar. Preferably, the medium is selected from the group consisting of cell culture or a test tube.

A method of screening for a drug useful in the treatment of Alzheimer's Disease, comprising the steps of: increasing the polymerization of tau peptides in a medium by contacting said culture with an effective amount of at least one unesterified fatty acid or a compound that induces fatty acid liberation and release; and testing a drug of interest to determine whether the drug inhibits the polymerization of tau peptides induced by the unesterified fatty acid. Representative examples of useful fatty acids include arachadonic acid, palmitoleic acid, oleic acid, linoleic acid and stearic acid. Preferably, the unesterified fatty acid is found in an amount from about 1 micromolar to about 100 micromolar. A represenative example of a compound that induces fatty acid liberation and release is melittin. Preferably, the melittin is found in amount of from about 0.1 micromolar to about 1.0 micromolar. Preferably, the medium is selected from the group consisting of cell culture or a test tube.

The following examples are given for the purpose of illustrating various embodiments of the invention and are not meant to limit the present invention in any fashion.

EXAMPLE 1

Brain Tissue

Fresh bovine brains were obtained from John Morrell Meat Packing, Montgomery, Ala. Fresh porcine brains were obtained from Bryan Meat Packing, Westpoint Miss. Human brain was provided by Dr. Richard Powers of the Brain Resource Center, University of Alabama at Birmingham. Sprague-Dawley rats were obtained from Charles River, Wilmington, Mass., and killed by decapitation. Purified neurofibrillary tangle (Iqbal et al., 1984) were provided by Dr. Khalid Iqbal, Institute for Basic Research in Developmental Disabilities, Staten Island, N.Y. Neurofilament antibodies (Amersham) and protein were provided by Dr. Robert Goldman, Northwestern University Medical School, Chicago, Ill.

EXAMPLE 2

Protein Purification

Microtubules were purified from brain by two cycles of temperature dependent assembly essentially as previously described (Shelanski et al., 1973), with glycerol added to 25% during the first warm incubation only. Tubulin was further purified by phosphocellulose chromatography (Weingarten et al., 1975), using phoshocellulose precycled as described (Sloboda et al., 1976). Taxol stabilized microtubules (Vallee, 1982) were made by incubating purified porcine tubulin at 5 mg/ml with 10 $\mu$M taxol for 30 minutes at 37° C., then diluting ½₀ for electron microscopy.

Tau was isolated using protocols similar to those published by others (Sandoval and Weber, 1980; Johnson et al., 1989), exploiting the protein's stability to heat treatment (Cleveland et al., 1977a) and solubility in perchloric acid (Lindwall and Cole, 1984). For isolation from microtubules, pellets were resuspended in cycling buffer (100 mM PIPES, 1 mM EGTA, 1 mM MgCl₂, pH 6.9) supplemented with 0.8 M NaCl and 2 mM DTT, stirred on ice for 30 minutes, boiled for 10 minutes, stirred on ice for 30 minutes, and centrifuged at 100,000 x g for 45 minutes. Supernatants were concentrated over an Amicon YM10 ultrafiltration membrane, and loaded on a Bio-Gel A-1.5 sieve column (32×430 mm, run at 15 ml/hour), equilibrated with buffer A (20 mM MES, 80 mM NaCl, 2 mM EGTA, 1 mM MgCl₂, 0.1 mM EDTA, pH 6.8) supplemented with 0.8 M NaCl and 2 mM DTT (buffer A+). Fractions containing tau were brought to 2.5% perchloric acid, stirred on ice for 30 minutes, and centrifuged at 100,000 x g for 30 minutes. Supernatants were dialyzed against buffer A, and concentrated by ultrafiltration. Residual DTT was estimated to be <0.2 $\mu$M. All procedures except boiling were carried out at 40° C.

For isolation of tau directly from whole brain, frozen tissue was thawed and homogenized (1:1 wt/vol) in a Waring blender in buffer A+ supplemented with an additional dry weight of NaCl sufficient to bring the homogenate to 0.8 M NaCl. Following centrifugation at 150,000 x g for 45 minutes, the supernatant was boiled 10 minutes, iced 30 minutes, and spun as above. The supernatants were then brought to 60% saturation with $(NH_4)_2SO_4$, stirred on ice 45 minutes, and spun. Pellets were resuspended in a total of 50 ml of buffer A+, dialyzed against the same solution, concentrated by ultrafiltration, and loaded on the sieve column.

Procedures described above for isolation of tau from microtubules were then followed.

EXAMPLE 3

Conditions for Tau Polymerization

In general, tau stored at −80° C. in buffer A was thawed at 4° C., diluted into 100 mM Tris pH 7.2 containing DTT or b-mercaptoethanol (bME), and incubated at 37° C. 100 mM MES was used for experiments requiring buffering below pH 7. Final tau concentrations were in the range of 1–10 µM. Significant variations in time, temperature, pH, ionic strength, and concentration of reducing agent were seen.

EXAMPLE 4

Electron Microscopy

Samples were deposited in 10 ml aliquots onto 400 mesh nickel grids coated with 0.4% formvar, rinsed with 5 drops $H_2O$, and stained with 5 drops of 2% uranyl acetate, the last drop sitting 1 minutes prior to blotting. Grids were examined using a JEOL JEM-100CX transmission electron microscope operated at 80 kV. For filament length measurements, micrographs obtained at a nominal magnification of 15K (FIG. 6) or 10K (FIGS. 7 and 9) were digitized using a SIT68 camera (MTI), and lengths were determined using software from Universal Imaging Corporation. Only filaments contained completely within a field and measuring at least 50 nm were included in data sets. Fields selected at random were chosen at low illumination and without the aid of the 10X binoculars, so that Formvar integrity could be assessed without viewing the filaments present. Filament width measurements were made manually using micrographs similar to those shown in FIG. 1F–K. Microtubules (24 nm assumed diameter, with 6–7 discernable protofilaments) were used for size reference.

For colloidal gold labelling, following deposition on grids and an $H_2O$ rinse, grids were inverted for 1 hour on a 10 ml drop of the primary antibody (Tau-2; Papasozomenos and Binder, 1987) diluted in borate saline (0.1 M $H_3BO_3$, 25 mM $Na_2B_4O_7$, 75 mM NaCl). Grids were rinsed with borate saline, inverted on a drop of secondary antibody (Ted Pella, diluted 1/125), rinsed with borate saline supplemented with 1.5 M NaCl, and stained with 2% uranyl acetate.

EXAMPLE 5

Electrophoresis

Proteins were separated by SDS-PAGE (Laemmli, 1970) and stained with Coomassie blue or transferred to nitrocellulose (Towbin et al., 1979). For western blotting, antibody and blocking (2% non-fat dry milk) incubations were performed in borate saline. Protein concentrations were determined using the method of Lowry after samples in Laemmli sample buffer were precipitated with 10 volumes of 10% perchloric acid, 1% phosphotungstic acid.

EXAMPLE 6

Polymerization of microtubule tau

Polymerization of microtubule tau was accomplished by diluting the purified protein into neutral Tris or MES buffers in which sulfhydryl reactivity was limited by the presence of reducing agents. Polymers formed under a variety of conditions are shown in FIG. 1. Polymerization was demonstrated using tau from juvenile rat (indicated by postnatal (P) age), adult rat, and adult pig, at protein concentrations of 1.6–6.5 µM. Incubations were done at 37° C. for 5–26 hours, using 5–25 mM bME or 2–20 mM DTT. These filaments resemble the straight filament known to reside within the neurofibrillary tangle, in the sense that they are non-helical and unpaired. The obvious flexibility of some filaments (FIG. 1D), however, makes them straight in a strictly non-Euclidean sense, and distinguishes them from the rather rigid appearing paire helical filament (Wisniewski et al., 1984) and straight filament (Crowther, 1991). The tau polymers at their widest extent have an average width of 10.5 nm, with a measured range of 6.5–13 nm. Filaments narrow for variable distances at irregular intervals (FIG. 1H,J) to about 50% of their widest extent. These narrowings may represent the crossover points of a slightly twisted filament. Straight filament isolated from neurofibrillary tangle also show a modulation of width interpreted as resulting from a twisting of the long axis (Crowther, 1991). The relatively large range of radial dimensions observed is believed to result from this variable twisting combined with the final disposition of filaments on the grid, and not from multiple filament morphologies. Differences in staining intensity which may create the appearance of multiple filament populations within a single field (FIG. 1A) are commonly observed. These are due to the unequal contributions of positive and negative staining across the grid surface, and do not indicate the presence of multiple filament morphologies.

Also shown in FIG. 1 are two types of aggregation often seen in preparations of polymerized tau. The first is most common in the juvenile tau samples, and appears to involve the precipitation of nonfilamentous tau onto tau filaments (FIG. 1B). Due to the electron opaqueness of these aggregates, the possibility that they are composed of highly compacted short filaments cannot be ruled out. They are, however, usually associated with a single discernable tau filament. The appearance of such aggregates is usually associated with an obvious decrease in the density of filaments seen by electron microscopy, and confounds attempts to quantify polymerization by centrifugal separation of soluble and filamentous tau. Bundling of tau filaments was also occassionally observed (FIG. 1C). Both forms of aggregation appeared to be reduced when the Tris assembly buffer was replaced with borate saline (data not shown), though this may reduce polymer yields.

Fifteen tau isolates were examined for their ability to form filaments. Though all of the tau preparations purified from twice-cycled microtubule exhibit the ability to assemble, none of the preparations purified directly from whole brain extracts exhibit this property. The assembly incompetent tau included isolates from bovine, porcine, and human brain. Tau purified by both methods is presumed to have the same primary structure, but is likely to exist in different states of phosphorylation due to the activity of phospatases and kinases present during microtubule cycling (Tsuyama et al., 1986; Burns, 1991). Differences in levels of specific post-translational modifications may be involved in stimulating or supressing polymerization.

EXAMPLE 7

Morphology of in vitro-assembled tau polymers

Figure 2:
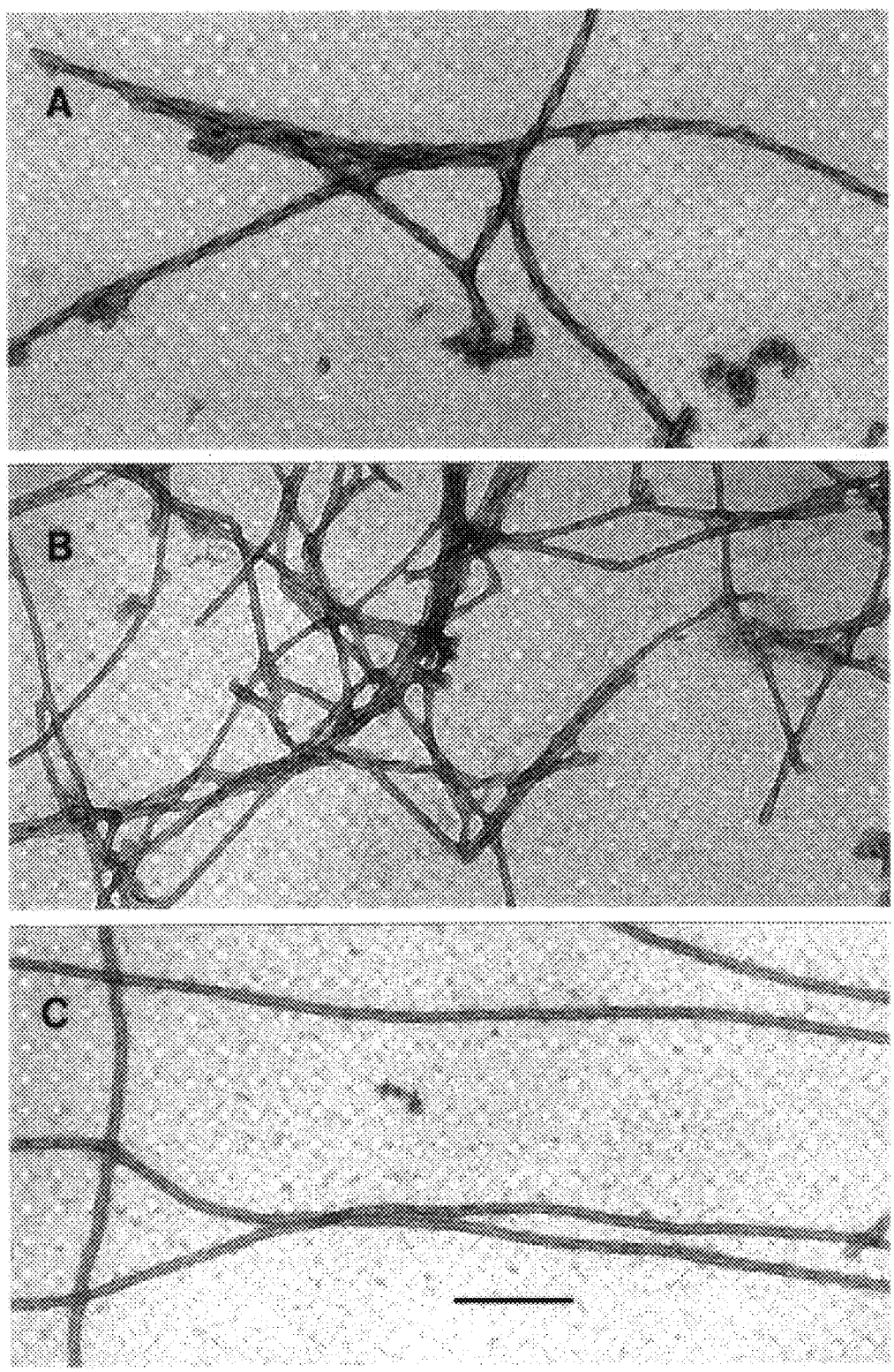
FIG. 2 shows the comparison of tau polymers assembled in vivo and in vitro. Purified neurofibrillary tangle (FIGS. 2A and 2B) and tau filaments (FIG. 2C) were stained with 2% uranyl acetate. Examples of both paire helical filament (FIG. 2A) and straight filament (FIG. 2B) are shown. Bar equals 0.2 μm.

The morphology of in vitro-assembled tau polymers was compared to that of Alzheimer's straight filament and paired helical filament (FIG. 2). Neurofibrillary tangles were isolated using an SDS extraction protocol (Iqbal et al., 1984), and processed for electron microscopy in the same manner as the tau filaments. Most of the filaments found in the neurofibrillary tangle preparation exhibited the typical paired helical filament morphology (FIG. 2A). Occassional straight filament were observed, and rarely, a neurofibrillary tangle fragment composed almost exclusively of straight filament was observed (FIG. 2B). A comparison of straight filament and tau filaments (FIG. 2C) revealed two filament populations which were similar in width and which presented a smooth surface lacking detectable substructure by this staining method. The paired helical filament at their widest extent were significantly wider than the straight filament or the in vitro-assembled tau filaments. The straight filament found in neurofibrillary tangles were apparently more rigid than tau filaments (FIG. 1D), and often appeared to be broken when forced by inter-filament contacts to attempt significant bending. This may result from straight filament containing a greater number of phosphorylated residues, analogous to the increased rigidity of paracrystals formed from phosphorylated tau (Hagestedt et al., 1989).

Figure 3:
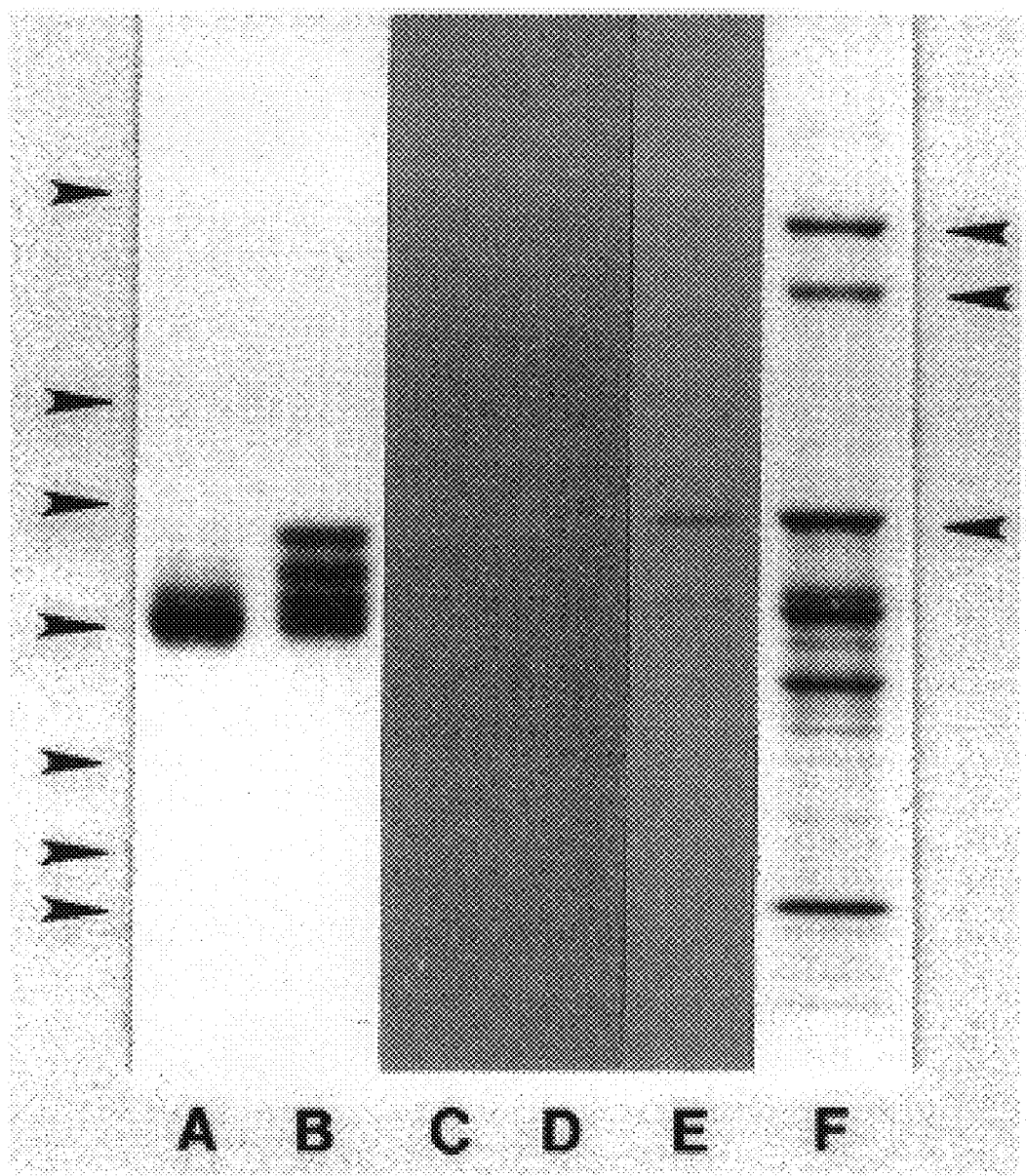
FIG. 3 shows the purification of tau to apparent homogeneity. (A–D) Microtubule tau from P14 rat (5 mg—A,C) or adult rat (10 mg—B,D) was separated on 4–20% gels and stained with Coomassie Blue (A,B) or blotted with a monoclonal antibody which binds the 68 kD neurofilament protein (C,D). Neurofilament protein was also blotted (40 ng—E) or stained with Coomassie Blue (15 mg—F). Molecular weight markers (in descending order; 208, 101, 71, 44, 29, and 18 kDa) are indicated to the left, and the neurofilament triplet proteins on the right. Lanes C–E were excised from the same blot.

Due to the fact that the polymers were also similar in size to neurofilaments, and that neurofilaments are a known contaminant of the cycled microtubule from which the assembly competent tau (Berkowitz et al., 1977) was purified, the tau isolates were examined for possible contamination by neurofilament proteins. A Coomassie stain of two typical tau preparations separated by SDS-PAGE revealed dye binding only to the tau bands (FIG. 3A, 3B). A western blot of an identical gel using a monoclonal antibody directed against neurofilament light chain showed binding to 40 ng of a partially purified neurofilament preparation (FIG. 3E; binding was also detected at 10 ng), but no binding to the tau proteins loaded at 5–10 µg/lane (FIG. 3C, 3D). The maximum potential neurofilament contamination was calculated to be <0.1%.

Figure 4:
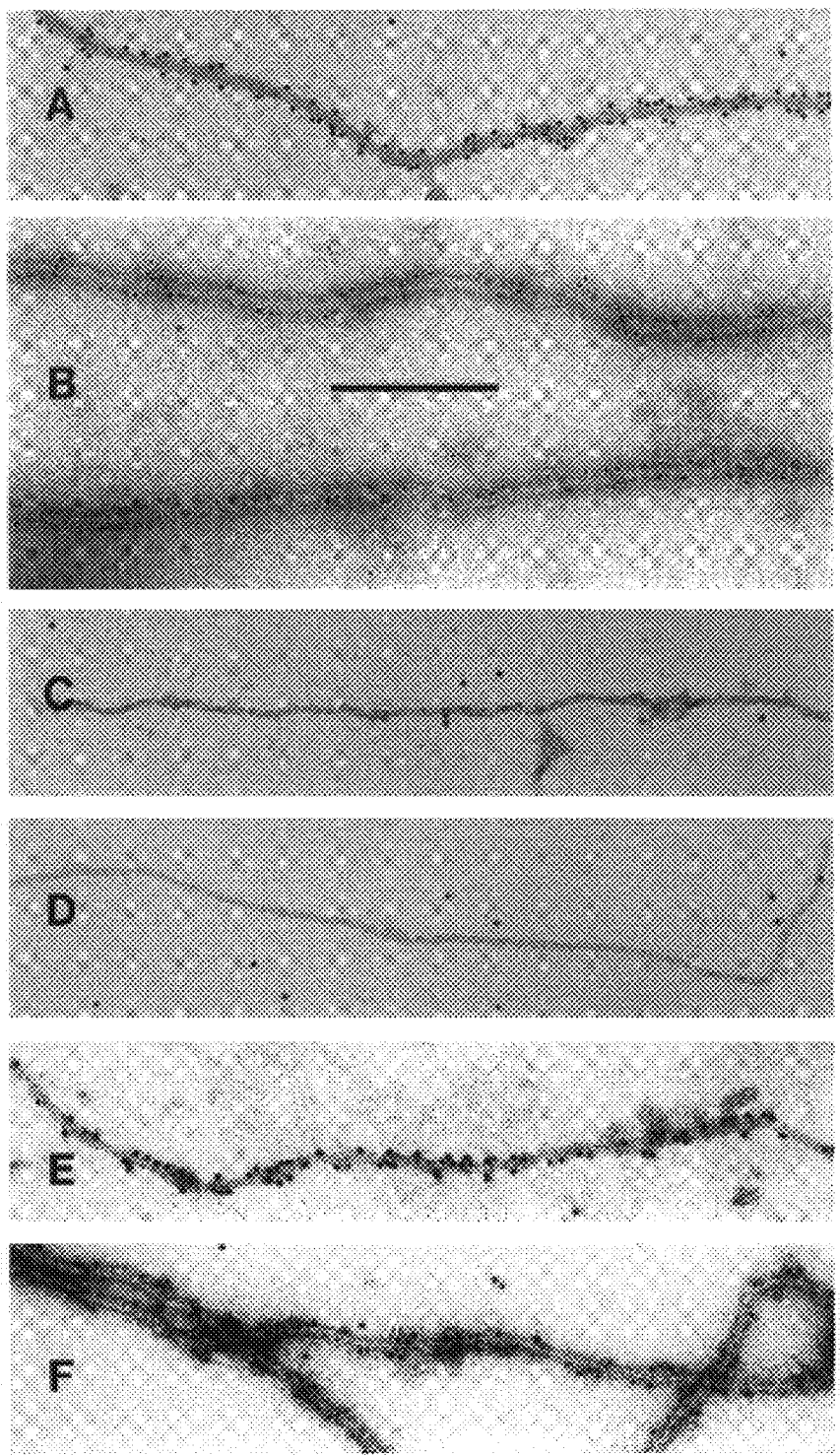
FIG. 4 shows the antibody labelling of tau polymers. Porcine tau was assembled overnight, and filaments were either deposited directly on grids (FIGS. 4A–D) or incubated in 500 mM KCl for 30 minutes at 37° C. prior to being deposited on grids (FIGS. 4E, 4F). Grids were then incubated with the tau monoclonal antibody, Tau-2 (FIGS. 4A, 4B, 4E, 4F), or control buffer (FIGS. 4C, 4D), followed by incubation with a secondary antibody conjugated to 10 nm colloidal gold. Grids were then stained with uranyl acetate. Two examples of gold labelling for each condition are shown. Bar equals 0.2 microns.

To further confirm that in vitro assembled filaments were composed of tau, EM localization was performed using a tau monoclonal antibody in conjunction with gold conjugated secondary antibodies. Gold particles were specifically associated with filaments when filaments were pre-incubated with the Tau-2 monoclonal antibody (FIG. 4A, 4B), but not when the primary antibody was omitted (FIG. 4C, 4D). Treatment of filaments with 0.5 M KCl to remove proteins bound nonspecifically to the surface of filaments did not affect labelling (FIG. 4E, 4F).

Figure 5:
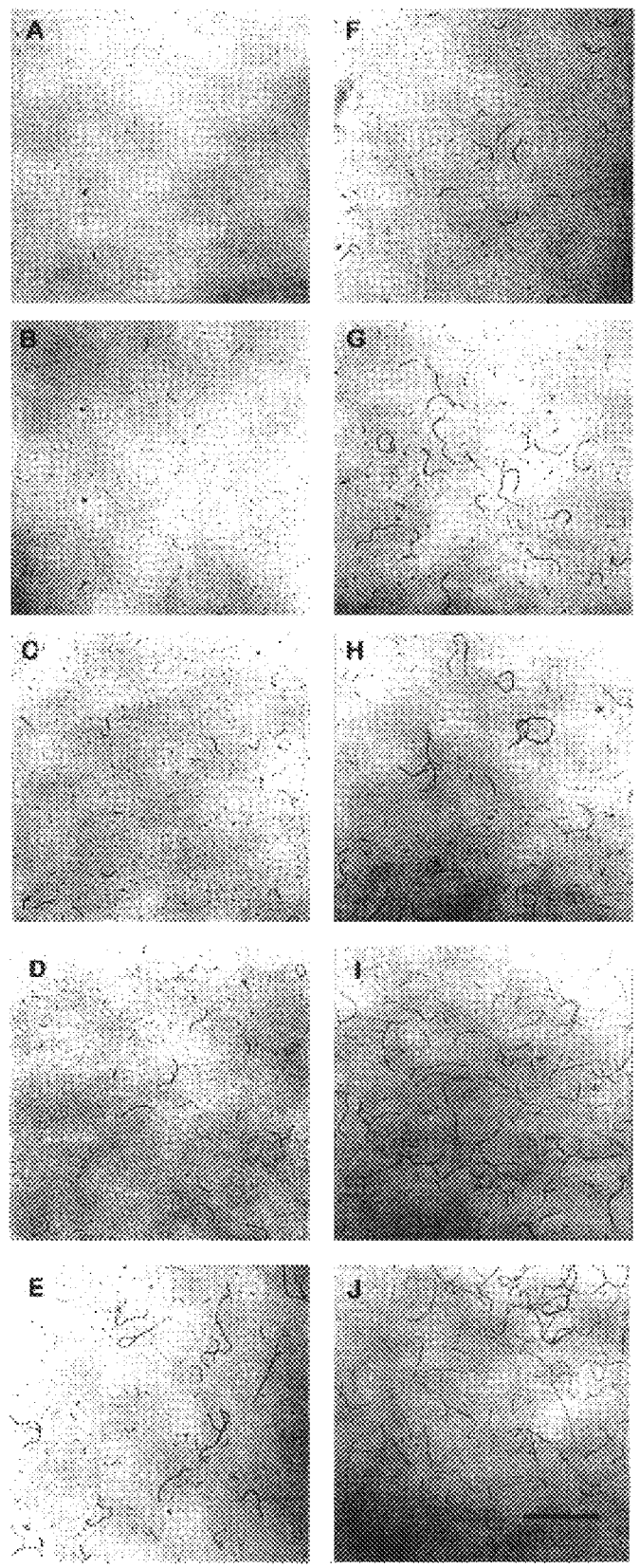
FIG. 5 shows the filament length is dependent on time and temperature. Tau purified from P14 rat microtubule was incubated in 10 mM DTT at 22° C.

Analysis of filament assembly revealed that the extent of polymerization was dependent on incubation times and temperatures (FIG. 5). Increasing incubation times resulted in the presence of longer filaments on the grid surface. When tau is incubated at 37° C. (FIGS. 5 F–5J), the filaments formed appear to be greater in length and number than those formed at 22° C. (FIGS. 5A–5E). In this preparation of P14 rat tau, no polymerization was evident after a 4 hour incubation at 4° C. In subsequent experiments with adult rat tau, however, some polymerization was observed at 4° C. (data not shown).

Figure 6:
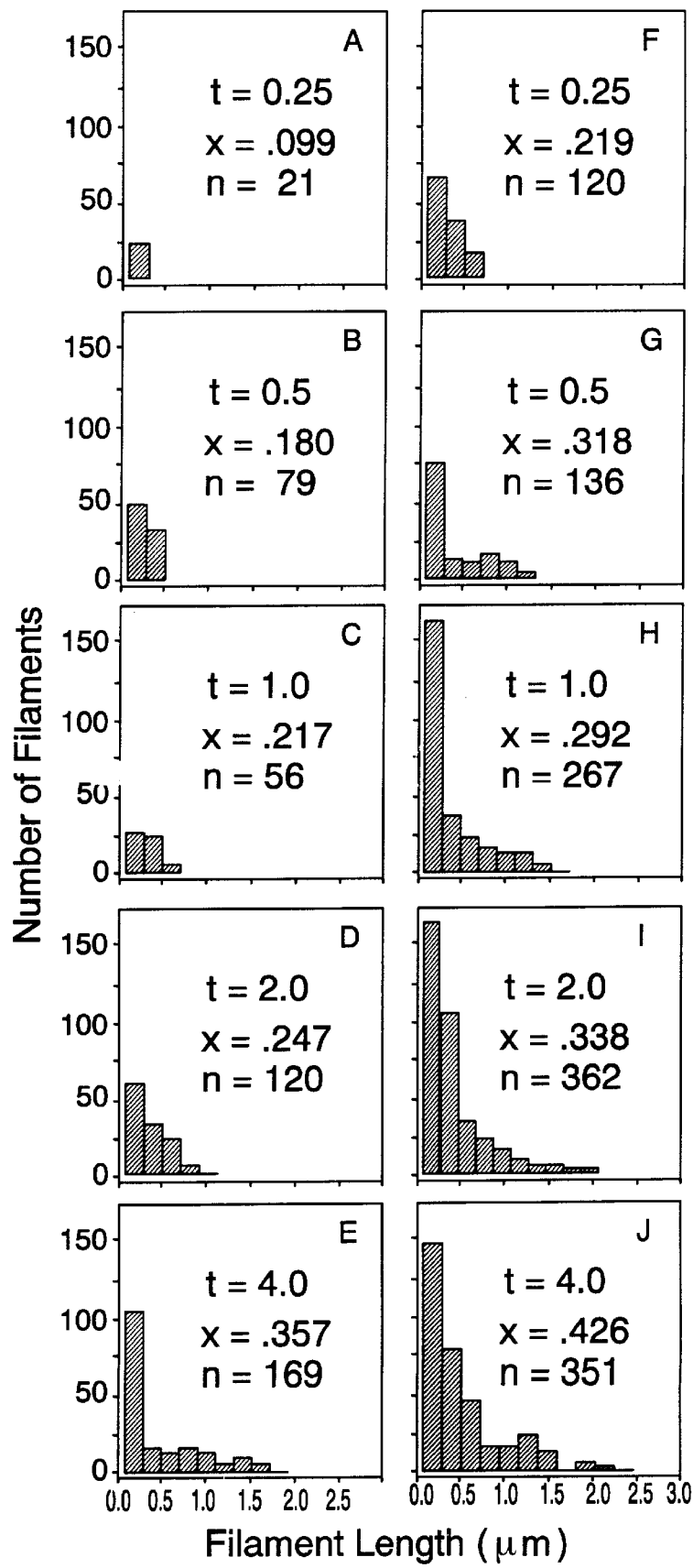
FIG. 6 shows that filament lengths display an exponential distribution. P14 rat tau was incubated in 10 mM DTT at 22° C.

Electron micrographs similar to those seen in FIG. 5 were digitized so that filament lengths could be measured (FIG. 6). The histograms generated confirm that the average filament length increases with time, and, at any given time, filaments in the 37° C. sample were longer. The data also show that filaments display an exponential distribution, rather than the Gaussian distribution that is usually seen in microtubule populations (Symmons and Burns, 1991). This type of distribution would be consistent with a filament population which was adding nucleation sites at a constant rate, and exhibiting limited subunit dissociation.

Figure 7:
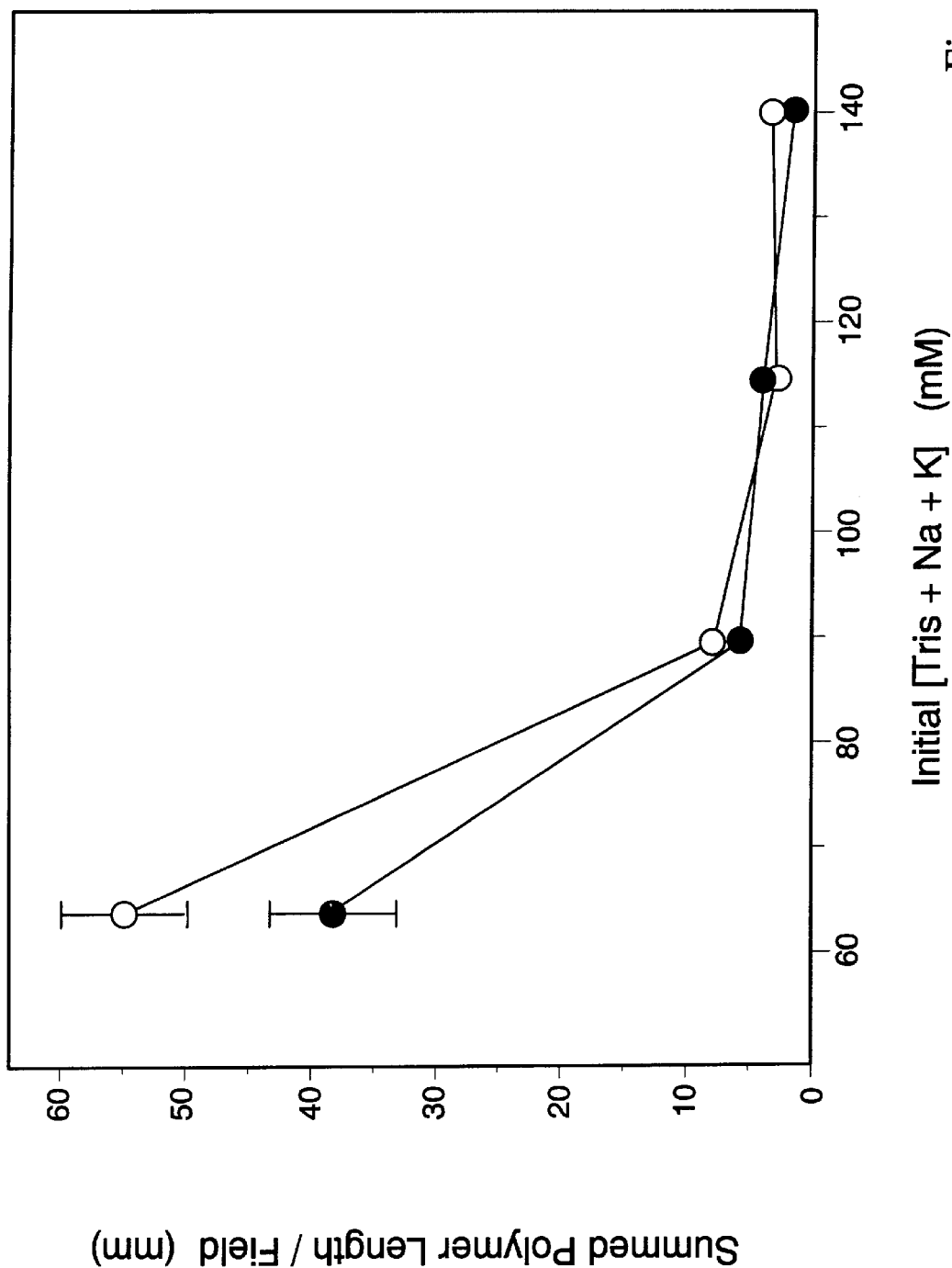
FIG. 7 shows the polymerization of tau filaments is dependent on ionic strength. Porcine tau in Buffer A was diluted 1:1 into neutral 50 mM Tris/20 mM DTT supplemented with a variable amount of KCl. Samples were incubated for 24 hours at 37° C. then supplemented with another 500 mM KCl. One aliquot was taken immediately for EM processing (open circles), and another after a further 24 hour incubation at 37° C. (filled circles). Random fields were digitized, then filaments were measured and their lengths were summed. The average total polymer length/field +/− S.E.M. is plotted as a function of the initial cation concentration, n>10.

The dependence of filament assembly on ionic strength was also examined. As neutral solutions (25 mM Tris, 40 mM NaCl) were supplemented with 0–75 mM KCl, the filament mass subsequently found on grid surfaces was markedly decreased (FIG. 7). All samples were supplemented with 500 mM KCl prior to their deposition on grids, so this decrease is not due to differential adherence to the grid surface which could have otherwise resulted from the variable salt content of the samples. Filaments were observed at low density when KCl was added at 100 mM (Tris+Na+K=165 mM), but complete inhibition was routinely observed at higher salt concentrations (data not shown).

With respect to filament depolymerization, increasing KCl concentrations well above assembly-inhibiting concentrations caused only limited filament disassembly. Filaments were still observed when samples preassembled for 24 hours were raised to over 500 mM KCl and incubated another 24 hours (FIG. 7). This suggests that assembled filaments display only limited subunit dissociation, consistent with the data obtained on filament length distributions (FIG. 6).

The effect of pH on tau polymerization is shown in Table 1. Tau from P14 and adult rat was incubated overnight in 20 mM bME buffered at variable pH then assayed for filament formation by electron microscopy. Assembly occurred over the broad pH range between 6 and 11, but was largely inhibited at pH 5.6 and completely inhibited at lower pH. Samples which were incubated overnight at inhibitory pH and then raised to neutral pH exhibited normal assembly (data not shown).

TABLE I

Tau polymerization is dependent on pH

| Tau source | pH for assay of filament assembly* | | | | | | | | |
|---|---|---|---|---|---|---|---|---|---|
| | 4.2 | 4.9 | 5.6 | 6.1 | 7.2 | 8.0 | 9.0 | 10.2 | 11.1 |
| d14 rat | — | — | +/−‡ | + | + | + | + | + | + |
| adult rat | — | — | +/− | + | + | + | + | + | + |

*Tau purified from microtubules was diluted 1:8 into 100 mM MES or Tris buffered at the indicated pH. Samples were incubated 16 hours at 37° C. in 20 mM BME, then viewed by electron microscopy.
‡Filaments were observed, but at very low density.

Figure 8:
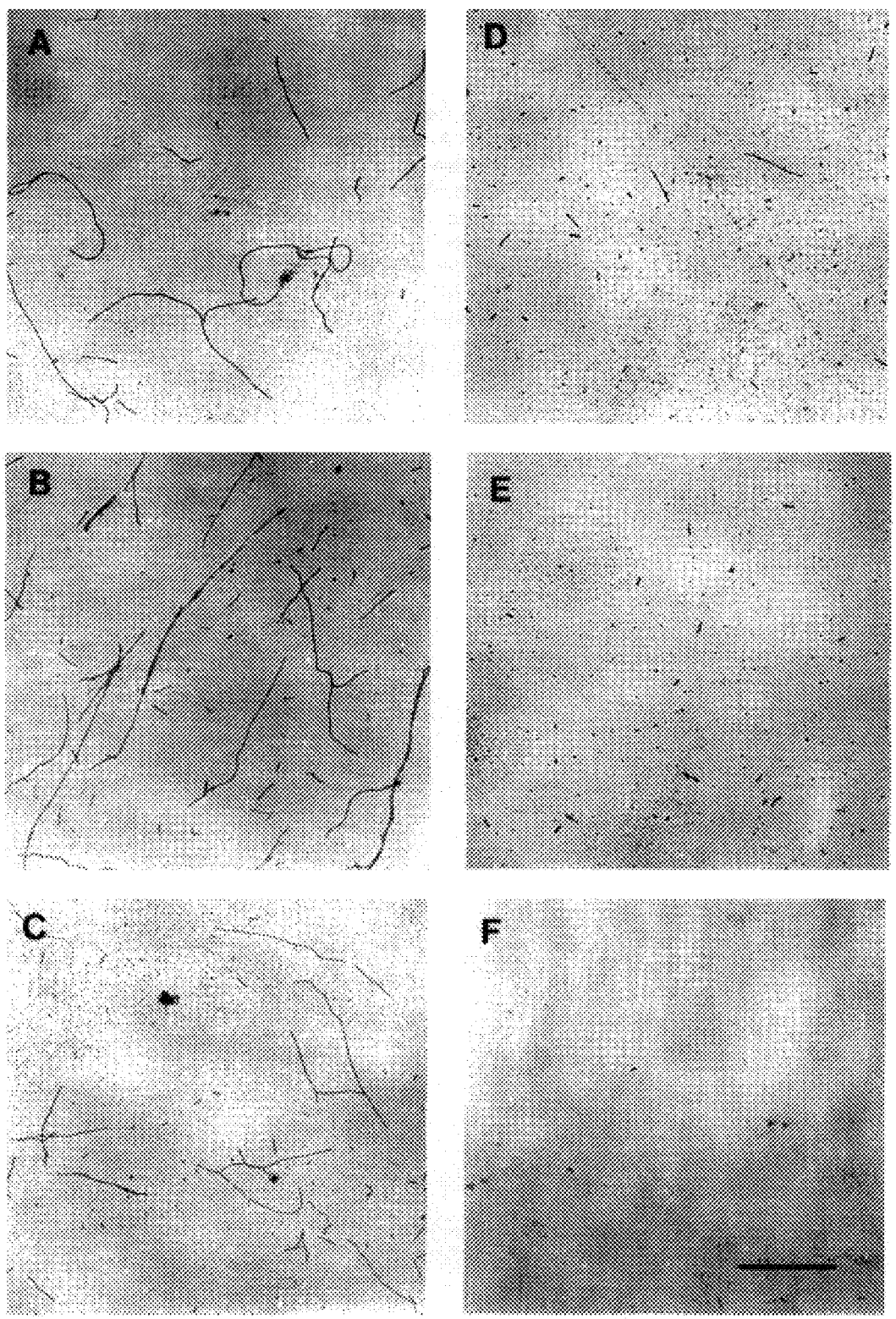
FIG. 8 shows that the tau polymerization is dependent on reducing potential. P14 rat tau was incubated overnight at pH 7.2 with bME added to 1.0 M (FIG. 8A), 0.1 M (FIG. 8B), 10 mM (FIG. 8C), 1.0 mM (FIG. 8D), 0.1 mM (FIG. 8E), or 0.0 mM (FIG. 8F). Samples were processed for EM, and representative fields are shown. Bar equals 1 micron.
Figure 9:
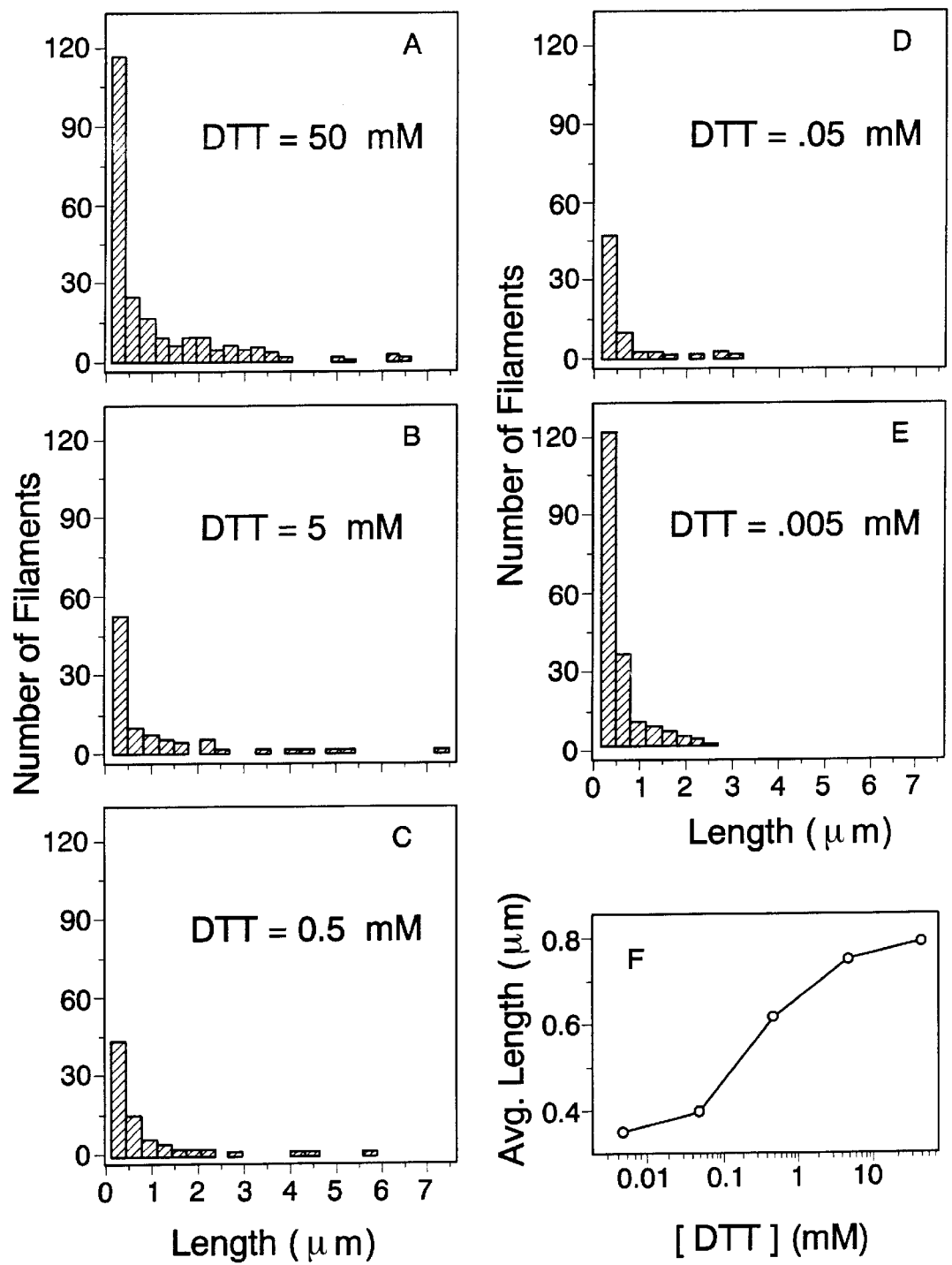
FIG. 9 shows that the filament lengths are a function of the reducing potential.

In earliest attempts at in vitro polymerization of P14 rat tau, it was readily apparent that reducing agents must be included in the incubation buffer if filaments of sufficient length to be recognized as such were to be formed. The relation between bME concentration and the length of filaments assembled from P14 tau is shown qualitatively in FIG. 8. As bME concentration was lowered from 0.1 M (FIG. 8B) to 0.1 mM (FIG. 8E), a decrease in maximum filament length was observed. At low bME concentrations, an increase in particles smaller than those recognized as filaments was often observed (FIGS. 8D and 8E). These may represent minimal length polymers. Similar data were produced using porcine tau and DTT as the reducing agent (FIG. 9). Although the average filament length clearly decreased as the concentration of DTT decreased (FIG. 9F), the length of filaments observed at the lowest level of reducing agent was more variable than that seen in other experiments (FIG. 8) with filaments as long as 2.4 microns recorded. This variation reflected the variable extent to which different preparations of microtubule tau were observed to polymerize, with those preparations which produced the highest level of polymer typically exhibiting a more uniformly short population of filaments at low concentrations of reducing agents. Although high concentrations of reducing agents were used in many experiments to maximize the assembly of long filaments, it should be emphasized that the range of reducing potentials represented in FIG. 9 would clearly encompass values expected to occur in the cytoplasm. Physiological concentrations of glutathione (1–10 mM, Hwang et al., 1992)—the tripeptide which constitutes most of the redox buffering capacity of the cytoplasm—also promoted the assembly of microtubule tau purified from P11 rat, adult rat, and adult porcine brain.

EXAMPLE 8

Protein Isolation

Sprague-Dawley rats were obtained from Charles River, Wilmington, Mass., and killed by decapitation at postnatal day 11 (juveniles) or at greater than six weeks of age (adults). Fresh porcine brains were obtained from Bryan Meat Packing, Westpoint Miss. Detailed protocols for the isolation of tau from whole brain or twice-cycled brain microtubules have been described above. Nonphosphorylated, recombinant human tau (htau40; Goedert et al., 1989) was the gift of Dr. Jeff Kuret, Northwestern University Medical School, Chicago, Ill. Recombinant tau was produced in $E.\ coli$ as a fusion protein with a polyhistidine tag, and purified to near homogeneity by nickel-chelate and gel filtration chromatography (Carmel et al., 1994). Following purification tau isolates were dialyzed against buffer A (20 mM morpholinoethanesulfonic acid pH 6.8, 80 mM NaCl, 2 mM EGTA, 1 mM $MgCl_2$, 0.1 mM EDTA) and stored at $-80°$ C. Protein concentrations were determined using the method of Lowry (Lowry et al., 1951), after samples in Laemmli sample buffer (Laemmli, 1970) were precipitated with 10 volumes of 10% perchloric acid, 1% phosphotungstic acid. Bovine serum albumin was used as the standard.

EXAMPLE 9

Preparation of Fatty Acids

All free fatty acids were purchased in the cis conformation and at maximum available purity from Sigma Chemical Company. free fatty acids were diluted into tau and amyloid samples from a 200X ethanolic stock, such that the final ethanol concentration in all samples and controls was 0.5%. Values for the critical micellar concentration (CMC) were obtained based on the phase partitioning of 10 mM phenyl-naphthylamine (Kovatcbev et al., 1981) when free fatty acids were diluted into assembly buffer.

EXAMPLE 10

Tau Protein Assembly

For most experiments, tau proteins were diluted to 2X the desired concentration in buffer A, then 1/2 in borate saline (0.1 M $H_3BO_3$, 25 mM $Na_2B_4O_7$, 75 mM NaCl) supplemented with 20 mM dithiothreitol (DTT) and 2X the required concentration of free fatty acids (final pH ~8.4). Assembly was performed at 37° C. in siliconized microfuge tubes. For evaluating the dependence of assembly on ionic strength, tau was diluted 1/10 into 111 mM Tris pH 7.2, 11 mM DTT, supplemented to give the indicated final concentrations of NaCl. At 250 mM NaCl, the measured CMC of arachidonic acid in the Tris buffering system was >2 mM.

EXAMPLE 11

Amyloid Peptide Assembly $A\beta_{1-40}$ (Amyloid β-protein, residues 1–40, Sigma) was resuspended in Aβ assembly buffer (100 mM Tris pH 7.4, 150 mM NaCl) at a concentration of 0.5 mg/ml, and frozen in aliquots at $-80°$ C. Thawed aliquots were diluted to 50 mg/ml in assembly buffer, and following a 2 hour pre-incubation, were centrifuged for 10 min at 14,000 rpm in an Eppendorf 5415C desktop centrifuge. The clarified solution was then supplemented with free fatty acids (final Aβ concentration ~10 mM), and incubated for 24 hours. Care was taken to perform all procedures at 4° C.

Fluorescence spectroscopy was performed essentially as described (Castano et al., 1995). Aliquots were diluted 1/6 into 67 mM glycine pH 9, 4 mM thioflavin T, vortexed, and placed in a quartz cuvette. Samples were read on a Perkin Elmer LS-50B luminescence spectrometer, excitation=435 nm, emission=485 nm, slit widths=5 nm. The integrated intensity was averaged from the initial ten, 10 sec sampling intervals. The signal was stable for at least several hours. The fluorescence of five samples lacking Aβ was averaged and subtracted as background from all readings. Free fatty acids did not contribute to the fluorescence signal over the range of concentrations employed.

EXAMPLE 12

Electron Microscopy

Samples were placed in 10 ml aliquots onto 400 mesh nickel grids coated with 0.4% formvar, for 1 minute. Tau samples were rinsed with 4 drops $H_2O$, and stained with 4 drops of 2% uranyl acetate, the last drop sitting 1 min prior to blotting. For staining of amyloid filaments, 4% uranyl acetate was used and the $H_2O$ rinse was omitted. Grids were examined using a JEOL JEM-100CX transmission electron microscope operated at 60–80 kV. For filament length measurements, random micrographs obtained at a nominal magnification of 15K were digitized and traced using either software from Universal Imaging Corporation or the public domain NIH Image program (for Macintosh; written by W. Rasband at the NIH and available from the Internet by anonymous ftp from zippy.nimh.nih.gov or on floppy disk from NTIS, 5285 Port Royal Rd., Springfield, Va. 22161, part number PB93–504868). Only tau filaments measuring at least 50 nm were included in data sets. Because short filaments were sometimes difficult to distinguish from background debri in digitized images, high concentrations of DTT were routinely used in order to maximize the production of longer filaments. Fields selected at random were chosen at low illumination and without the aid of the 10X binoculars, so that Formvar integrity could be assessed without viewing the filaments present.

EXAMPLE 13

Fatty Acid Dependence of Tau Assembly

Figure 10:
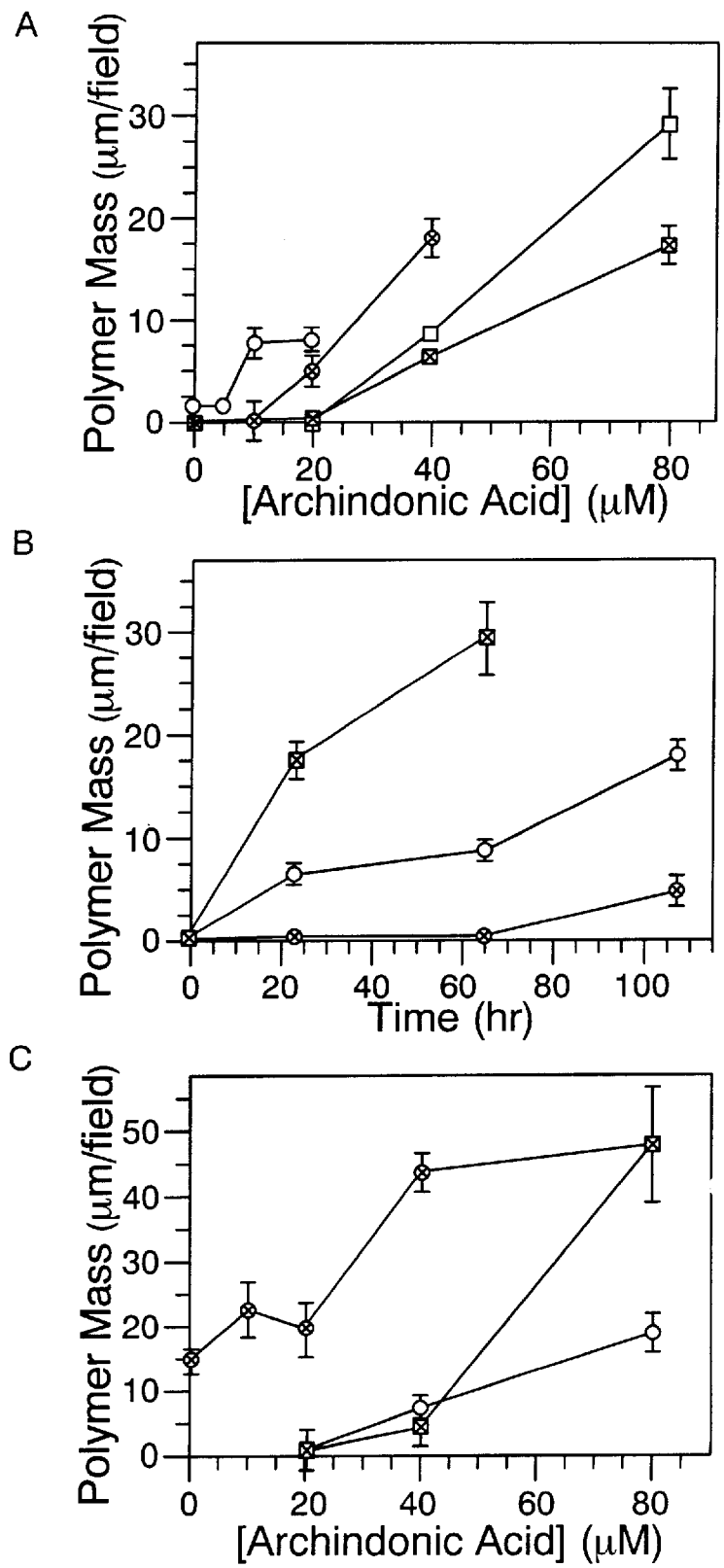
FIG. 10 shows the arachidonic acid dependence of tau assembly.

Using an assembly system, arachidonic acid (5,8,11,14-eicosatetraenoic acid) was observed to stimulate the polymerization of all tau preparations examined. Juvenile MTτ, which is uniquely comprised of the smallest of the six tau isoforms produced in adult brain (Lee, 1990), assembled in a dose dependent manner (FIG. 10A). The apparent threshold for stimulation was a function of time, and was less than 10 μM at the longest timepoint tested. When the data in FIG. 10A are replotted such that the polymer mass is expressed as a function of time (FIG. 10B), the curves generated are essentially linear with no evidence of plateauing, indicating that the rate of assembly is relatively constant up to 66 hours (80 μM), 108 hours (40 μM), or 214 hours (20 μM). Arachidonic acid also stimulated the polymerization of adult rat MTτ (FIG. 1C). This preparation exhibited a greater potential for spontaneous assembly than juvenile MTτ, and larger absolute increases in polymer formation at arachidonic acid levels of 10–40 μM. Juvenile MTτ, however, displayed a larger percent increase in assembly when stimulated by 40–80 μM arachidonic acid. Under the same conditions, no spontaneous assembly was exhibited by human recombinant tau and tau purified from porcine whole brain. Filaments were observed, however, when these tau preparations were incubated with 20–80 μM arachidonic acid (FIG. 10C). Although levels of spontaneous and inducible assembly varied between the different tau preparations, the source of this variance could not be determined due to differences in the concentration of protein employed (100–200 μg/ml), levels of posttranslational modification, and species specific differences in amino acid sequence.

In order to determine which free fatty acids could most effectively be used as inducers of tau assembly, the stimulatory effects of free fatty acids that differed in the length of their carbon chain and extent of saturation were examined. In general, for any given chain length tested, unsaturated free fatty acids were more potent than saturated free fatty acids (Table II-FIG. 12). A 20–30 fold increase in polymer formation was observed when using 50 μM arachidonic, palmitoleic, or linoleic acid. The stimulatory effects of free fatty acids were not due to localized concentrations of surface charge produced by fatty acid aggregation, as measurement of the CMC of some representative free fatty acids indicates that they were effective at concentrations below this value (Table II-FIG. 12). Based on the qualitative examination of grids, tau assembly did not appear to be stimulated by the methyl or ethyl esters of arachidonic acid, which were also utilized at 50 μM (below their measured CMC values).

TABLE II

Tau polymerization induced by different free fatty acids.*

| Fatty Acid | Polymer Mass (μm/field) | % max-imum | CMC (mM |
|---|---|---|---|
| control (no f.a.) | 0.63 ± 0.17 | 3 | |
| 5,8,11,14,17-eicosapentaenoic acid (20:5) | 11.81 ± 1.51 | 48 | NA† |
| 5,8,11,14-eicosatetraenoic acid (20:4) | 24.51 ± 2.58 | 100 | 0.16 |
| 8,11,14-eicosatrienoic acid (20:3) | 7.99 ± 1.55 | 33 | NA |
| 11,14-eicosadienoic acid (20:2) | 1.20 ± 0.32 | 5 | NA |
| 11-eicosenoic acid (20:1) | 8.23 ± 1.36 | 34 | NA |
| 9,12,15-linolenic acid (18:3) | 4.01 ± 0.72 | 16 | NA |
| 9,12-linoleic acid (18:2) | 14.74 ± 3.31 | 60 | 0.21 |
| 9-oleic acid (18:1) | 7.36 ± 1.77 | 30 | 0.59 |
| stearic acid (18:0) | 3.60 ± 0.54 | 15 | >1 |
| 9-palmitoleic acid (16:1) | 23.69 ± 4.11 | 97 | 0.44 |
| palmitic acid (16:0) | 7.37 ± 0.92 | 30 | NA |
| myristic acid (14:0) | 5.50 ± 0.76 | 22 | >1 |

*Tau filaments were assembled using juvenile rat MTτ. Samples were incubated for 72 hours in the presence of 50 μM free fatty acids. Polymer mass is expressed as the average ± S.E.M. (n = 12), or relative to the maximal assembly achieved with arachidonic acid.
†Data not available

EXAMPLE 14

Characteristics of Fatty Acid Induced Tau Polymers

Figure 11:
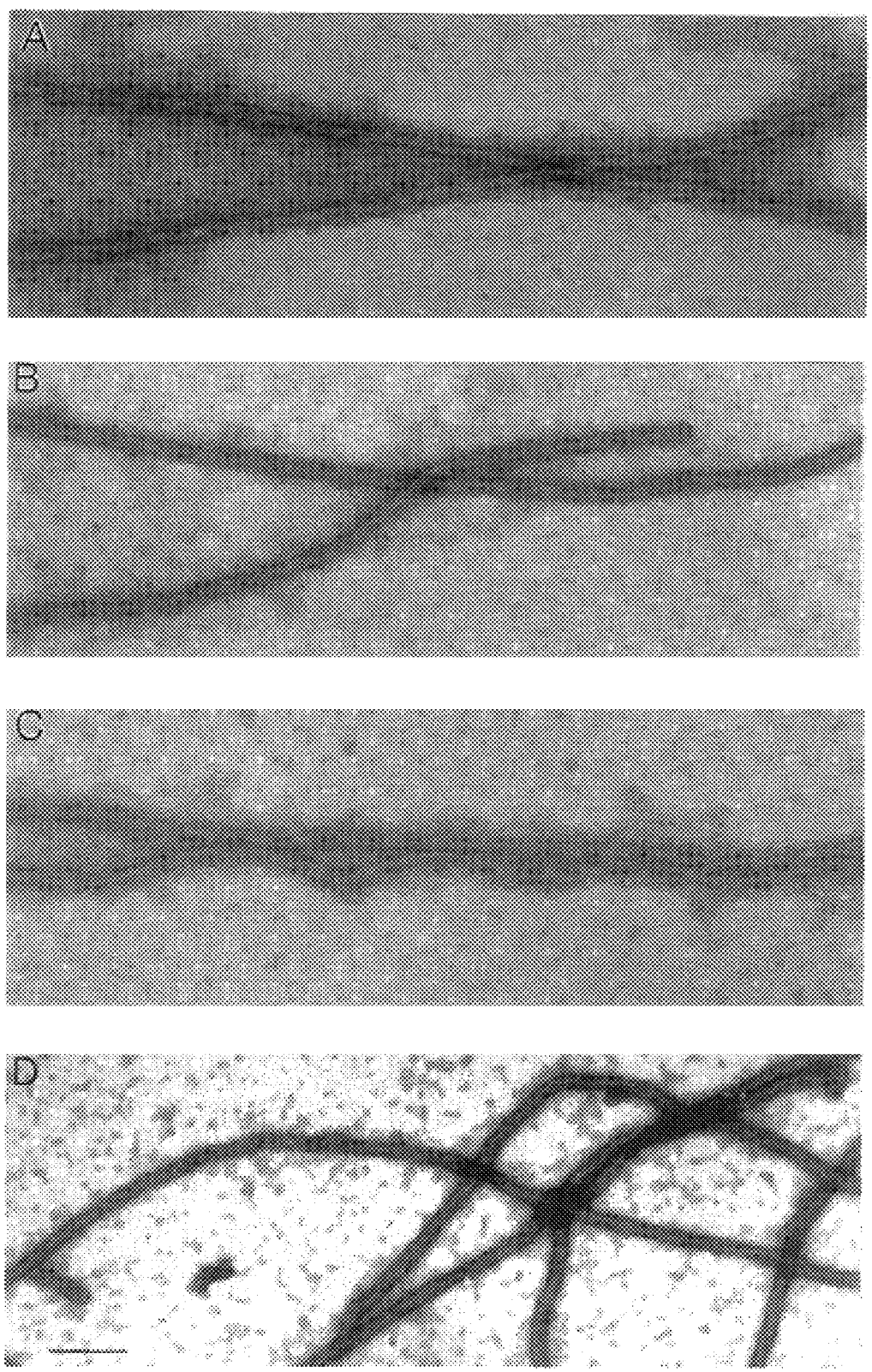
FIG. 11 shows the morphology of tau filaments formed in the presence or absence of arachidonic acid. Tau polymers were assembled using adult rat MTt (FIGS. 11A, 11B), porcine whole brain tau (FIG. 11C), or human recombinant tau (FIG. 11D). Samples were incubated for 72 hours in the absence (FIG. 11A) or presence (FIGS. 11B–D) of 50 µM arachidonic acid. Bar=100 nm.

The addition of free fatty acids to tau samples appears to modulate the rate of assembly but not the nature of the polymers formed. Filaments assembled from MTτ in the absence of free fatty acids (FIG. 11A) are indistinguishable from those assembled in the presence of 50 μM arachidonic acid (FIG. 11B). Filament morphology did not appear to vary when the source of purified tau was porcine whole brain (FIG. 11C), or human recombinant tau (FIG. 11D).

Figure 13:
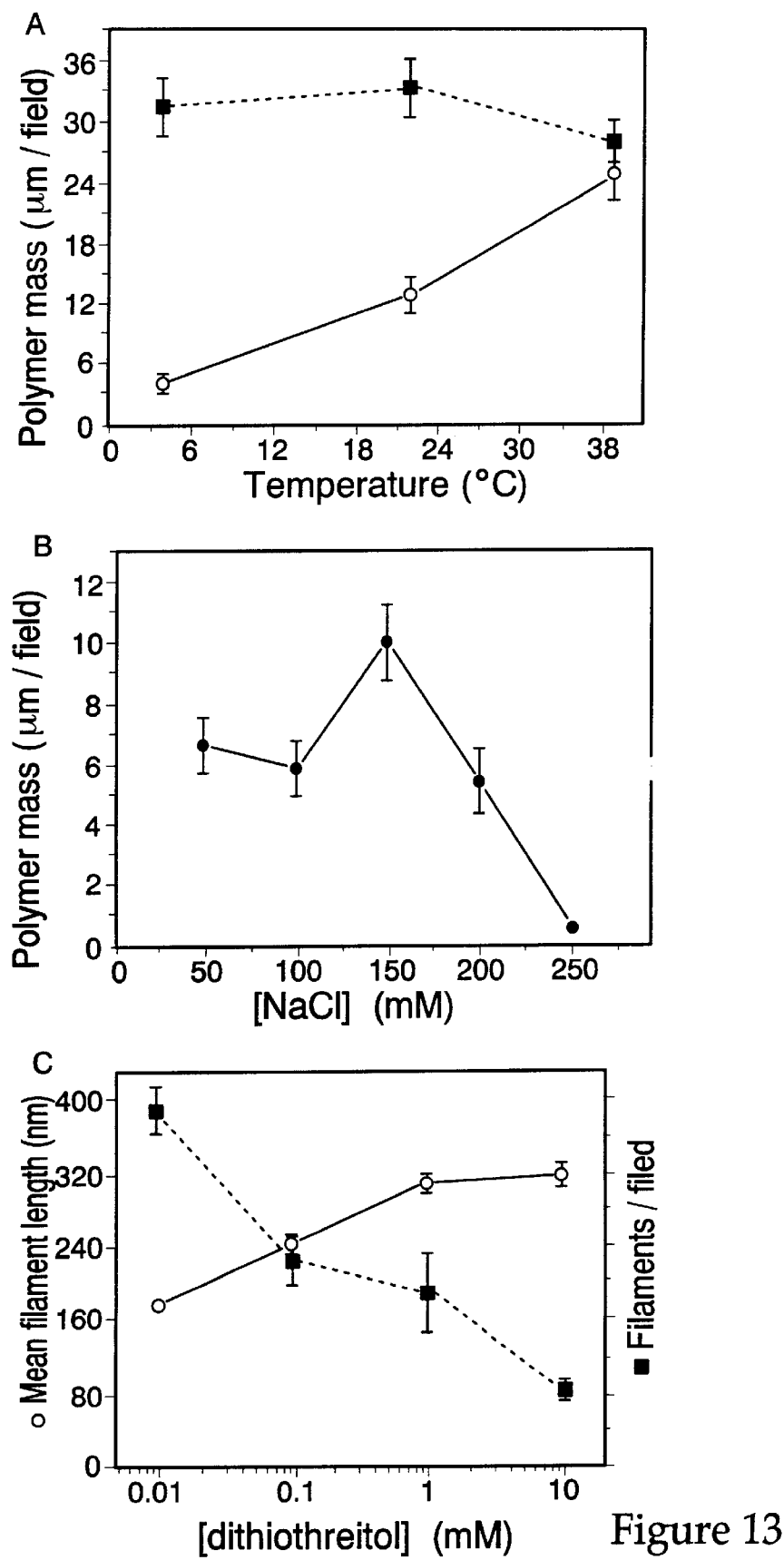
FIG. 13 shows the modulation of tau polymerization in the presence of arachidonic acid. All samples contained 100 µg/ml rat MTt and 50 µM arachidonic acid, and were incubated for 72 hours. Electron micrographs of negatively stained samples were digitized and traced, and the polymer content was expressed as total mass (FIG. 13A and FIG. 13B) or as mean filament length and number of filaments/field (FIG. 13C). In all cases values shown are the mean +/– S.E.M., n=12.

The polymerization of tau filaments in the presence of 50 μM arachidonic acid was dependent on temperature, ionic strength, and reducing potential, as was previously demonstrated for polymerization in the absence of free fatty acids, supporting the conclusion that filament structure is not altered by free fatty acids. Juvenile MTτ exhibited an approximately 500% increase in assembly when the temperature was raised from 4° C. to 37° C. (FIG. 12A). The assembly of adult MTτ was not dependent on temperature (FIG. 13A), however, indicating again that adult specific amino acid sequences and/or states of posttranslational modification are altering thermodynamic parameters of the assembly process. Concentrations of NaCl near 150 mM appeared to be optimal for the polymerization of adult MTT, while higher concentrations were inhibitory (FIG. 13B). This differs somewhat from earlier findings demonstrating inhibition at salt (NaCl+KCl) concentrations of only 65 mM, suggesting that free fatty acids shift the ionic strength dependence closer to a physiologic optima. Assembly of adult MTτ was also a function of the reducing potential (FIG. 12C). The increase in average filament length produced by increasing the concentration of DTT was accompanied by a decrease in the total number of filaments. Finally, assembly of adult and juvenile MTτ in the presence of 50 mM arachidonic acid was completely inhibited below pH 6, and all filament populations analyzed exhibited an exponential distribution of filament lengths, consistent with data generated in the absence of free fatty acids.

EXAMPLE 15

Fatty Acid Dependence of Amyloid Assembly

Given the concomitant appearance of tau and amyloid pathology in the AD brain, it was determined whether Aβ assembly could also be stimulated by free fatty acids. Oleic and linoleic acid, which comprise 45% of the unsaturated fatty acid content of the CSF, were chosen for these experiments because unsaturated free fatty acids appeared to more effectively induce tau assembly. Conditions were chosen in which spontaneous assembly of the Aβ would be expected to be minimal, in order to optimize the ability to detect free fatty acids dependent polymerization. For similar reasons, Aβ$_{1-40}$ was chosen for use in these studies, rather than the longer, more rapidly aggregating Ab variants. Following a two hour pre-incubation and a brief clarifying spin, peptide solutions examined by electron microscopy were characterized by the presence of relatively short (<0.5 mm) filaments dispersed individually or in small aggregates across the grid surface (FIG. 14A). When samples were incubated for 24 hours in the absence of free fatty acids, filaments were more aggregated and exhibited a moderate increase in length (FIG. 14B).

Figure 14:
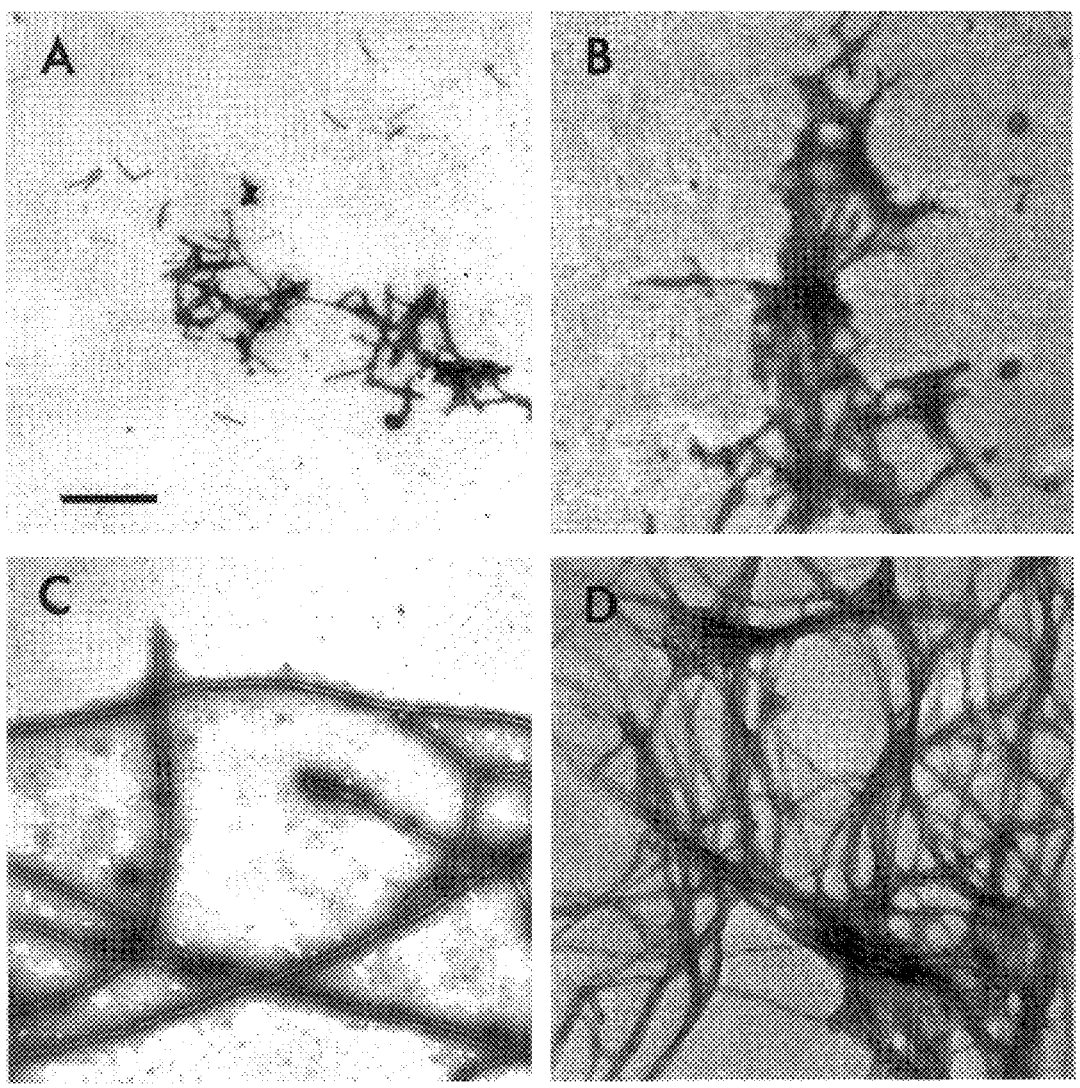
FIG. 14 shows the fatty acid dependent assembly of amyloid: Electron microscopy.

In contrast, when samples were incubated with oleic or linoleic acid, a dramatic increase in filament lengths was observed (FIGS. 14C and 14D). Filament widths were on the order of 5–10 nm, similar to values reported for other in vitro assembled amyloid fibrils (Burdick et al., 1992; Castano et al., 1995). If the Aβ concentration was increased from 10 μM to 25 μM, there was a considerable increase in the spontaneous formation of amyloid filaments, making the relative contribution of free fatty acids difficult to assess. Due to filament aggregation and the non-uniform dispersal of such aggregates on the grid surface, filament densities observed in FIG. 14 are not necessarily indicative of filament densities in solution. When preparing amyloid samples for electron microscopy it was necessary to limit assembly incubations to 24 hours or less, because larger aggregates formed at longer incubation times tended to collapse the Formvar or get washed off the grids during the staining procedure.

Figure 15:
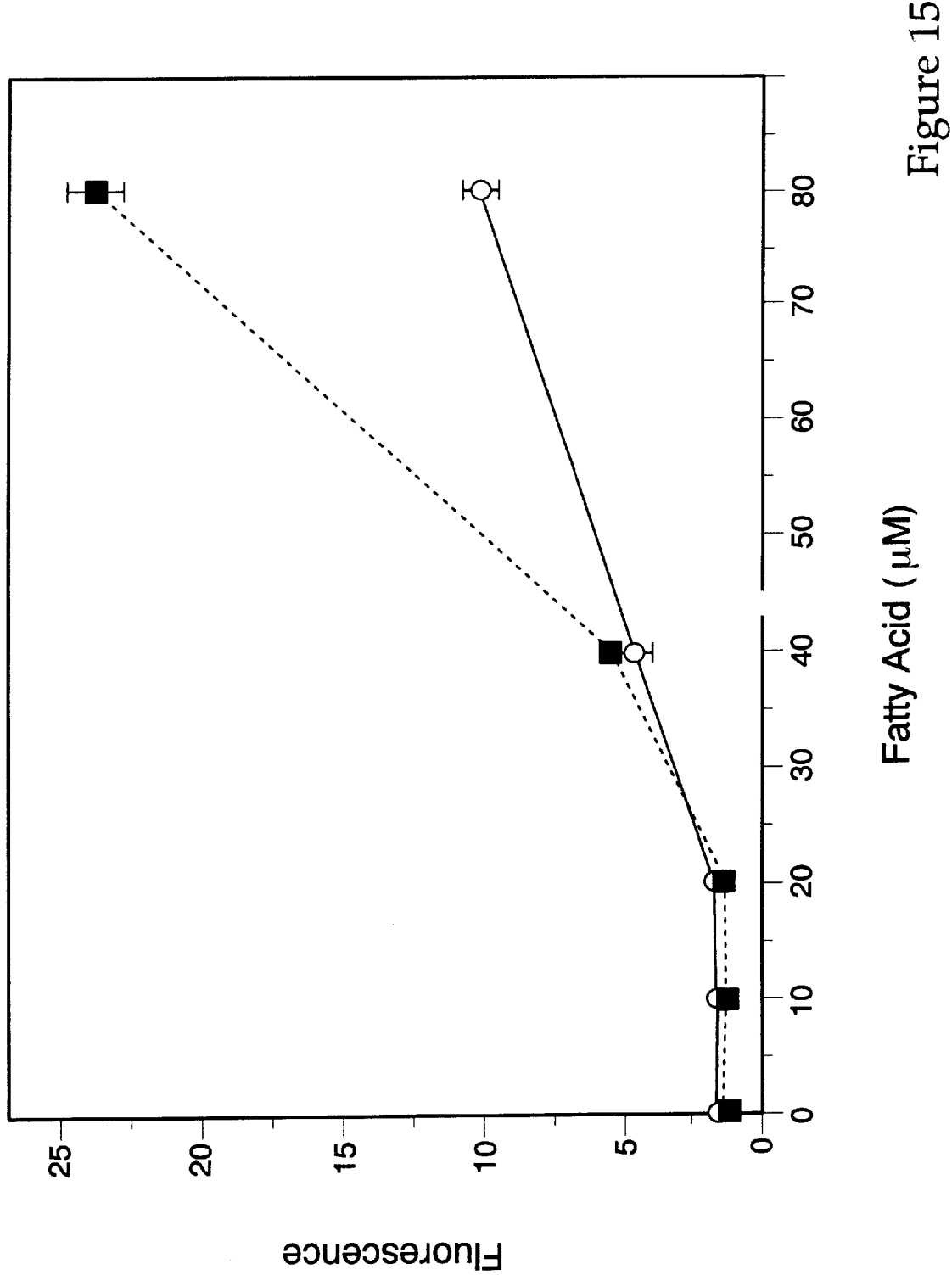
FIG. 15 shows the fluorescence spectroscopic analysis of amyloid assembly. Amyloid peptide was incubated for 24 hours with the indicated concentration of oleic (open circles) or linoleic acid (filled squares). Fluorescence values (arbitrary units) obtained after mixture with thioflavin T are shown as the mean±S.D., n=3.

Although free fatty acids appeared to have a pronounced effect on filament elongation, microscopic methods alone could not ascribe this to an induction of subunit incorporation: filament elongation could result from the lateral or endwise annealing of the short filaments observed in the absence of free fatty acids. A fluorometric assay was therefore employed as a measure of the total polymer mass present in peptide solutions. This assay is based on a unique excitation and emission maxima that results from the binding of thioflavin T to the β-sheet structure of proteins (Naiki et al., 1989; LeVine, 1993). Quantitative results obtained by this method were consistent with observations made by electron microscopy. The fluorescence signal indicated low levels of polymer formed in the absence of free fatty acids, and no increase above baseline in the presence of 10–20 μM free fatty acids (FIG. 15). Significant increases in the polymer content were observed at oleic and linoleic acid concentrations of 40 μM. At higher concentrations of free fatty acids, linoleic acid was distinguished as the more potent inducer of amyloid assembly. This demonstration of an increase in total polymer mass induced by free fatty acids indicates that filament elongation cannot be solely attributed to the annealing of pre-existing filaments, but rather must involve the further incorporation of peptide subunits. It is noteworthy that the polymerization of amyloid and tau filaments was stimulated by similar concentrations of free fatty acids, as would be expected if the dual processes of NP and NFT formation share a common effector molecule.

EXAMPLE 16

The present invention demonstrates, in one embodiment, the successful assembling of a homogenous population of tau filaments which appear to be morphologically related to the straight filament seen in Alzheimer's disease. It has not previously been demonstrated that tau will form polymers of this nature under conditions typical of the intracellular environment. Previous studies describing the assembly of tau filaments possessing straight or paired helical morphologies (widths ranging from 10–25 nm) have depended on the use of non-physiological conditions. Assembly of bovine or porcine tau was previously achieved only after the chemical (Montejo de Garcini et al., 1986) or enzymatic (Dudek and Johnson, 1993) modification of the protein. Assembly of recombinant tau constructs containing either the complete or partial tau sequence, relied on either high salt concentrations (1.25 M $CH_3CO_2$-$K^+$; Crowther et al., 1994), or an acidic pH (Wille et al., 1992, Crowther et al., 1992). None of these previous studies utilized reducing agents in their assembly reactions. In a reducing environment, the assembly of 10 nm tau filaments occurs when the variables of temperature, pH, and ionic strength were adjusted to physiological values. Of these variables, only ionic strength was limiting at physiological values, with optimal assembly occurring at lower salt concentrations. Although filament densities observed at physiological ionic strength were low, significant polymer mass might accumulate in situ on a longer time scale associated with the pathogenisis of the disease state.

Tau polymers formed in vitro, as well as straight filament formed in vivo, are ribbon-like in the sense that in cross-section their width is about twice their thickness, and that their measured profile depends on the extent to which they are lying either flat or on edge. Consistent with this interpretation is the two-fold difference in the range of widths measured for tau filaments. An example of a filament probably laying partially on edge is seen in FIG. 1J, where the central segment is very narrow but the ends are seen to flare to more typical dimensions. This interpretation of the filament morphology implies that the actual maximun width of these tau polymers is closer to the range maximum (13 nm) than the average measured width (10.5 nm). Although values of 15 nm reported for the width of straight filament in thin sectioned tissue are somewhat greater (Metuzals et al., 1981; Yagishita et al., 1981), overestimates due to the deposition of positive stain may result from this technique (Ruben et al., 1993).

Due to their similar dimensions, the possibility that the polymers assembled from the tau preparations were actually neurofilaments was addressed. Coomassie stained gels of representative tau samples revealed no neurofilament or other protein contaminants, and western blots of the same samples revealed no proteins cross-reactive with an anti-neurofilament protein antibody. The polymers formed were heavily labelled by an anti-tau antibody, even after incubating filaments in high salt to remove peripherally bound proteins. There were also differences between assembly conditions described herein and those previously reported for the assembly of neurofilaments. The assembly of tau filaments was favored at low ionic strength and inhibited at high ionic strength, while neurofilaments are assembled at high ionic strength (Geisler and Weber, 1981) and disassembled at low ionic strength (Hisanaga and Hirokawa, 1988). In addition, lowering the temperature or raising the pH of buffers used for filament assembly had no effect on the morphology of tau filaments (data not shown), but resulted in the formation of neurofilaments exhibiting abnormal morphologies (Aebi et al., 1988).

Following the time course of polymerization at different temperatures reveals three points of interest. First is the observation that all filament populations exhibited an exponential distribution of filament lengths, a fact confirmed by the length distributions generated over a range of DTT concentrations. This type of distribution is in contrast to the Gaussian distributions observed in equilibrated microtubule populations (Symmons and Burns, 1991), and is consistent with a filament population which exhibits limited subunit dissociation and adds nucleation sites at a constant rate. This interpretation is supported by the observation that tau filaments incubated at salt concentrations sufficient to inhibit assembly displayed only limited disassembly, again suggesting a relatively slow rate of subunit dissociation. A second point of interest is that the polymer mass formed increases as the temperature increases. This parallels the results of circular dichroism studies which demonstrated that the secondary structure content of tau also increased as a function of temperature (Ruben et al., 1991). It is likely, therefore, that prior to polymerization the tau molecule assumes a more highly ordered conformation. The third point is that tau filaments appear to lengthen with time while maintaining constant radial dimensions. This suggests that filaments are elongating by the endwise addition of subunits, as apposed to the lateral condensation of preformed protofilaments. This was not evident in previous studies which have all examined polymers from single time points.

A role for tau dimers in the assembly of paired helical filament-like polymers has previously been suggested (Wille et al., 1992). Treatment of tau constructs with phenylenedimaleimide to induce non-reducible cross-linking of cysteine residues resulted in the formation of tau dimers as demonstrated by SDS-PAGE, and these dimers assembled to form filaments identical to those formed by untreated tau (Wille et al., 1992). The observation that filament lengths decrease as bME or DTT concentration decreases suggests that tau dimers forming in a less reducing environment may inhibit the polymerization process. It has previously been shown in microtubule populations, however, that a factor which stimulates assembly (microtubule-associated proteins) reduces the average microtubule length (Sloboda et al., 1976). This illustrates the inverse relationship which can exist between assembly rate and filament length. Though disulfide bonds resistant to cytoplasmic reduction were found in globular proteins, they were not expected in a protein like tau which is believed to exist in an extended conformation with limited secondary structure (Cleveland et al., 1977b, Hirokawa et al., 1988). Since the region of tau which contains the cysteine residues is known to be a relatively hydrophobic part of the molecule (Ruben et al., 1991), however, conformational changes may be associated with dimerization and/or polymerization trap the relevant cysteines in a central hydrophobic domain not easily accessed by reducing agents.

The involvement of disulfide bonds may also be indicated by the pH dependence of assembly (Table I). The inhibition of assembly seen below pH 6.0 could be due to decreased sulfhydryl reactivity, though in this pH range effects due to histidine protonation cannot be ruled out. The assembly of tau deletion mutants was also observed to be pH dependent. Under non-reducing conditions, constructs encompassing most of the microtubule binding domain were not observed to assemble at neutral pH, but did form filaments at pH 5.0–5.5 (Wille et al., 1992) or pH 4.5–5.0 (Crowther et al., 1992). Under non-reducing conditions, tau preparations which do not form filaments of significant length at neutral pH (FIG. 8F), will form long filaments at pH 5.5 (data not shown). Taken together these data suggest that, although a sufficiently low pH will completely block polymerization, under conditions more conducive to assembly the effects of pH and reducing agent on disulfide stability are additive, and increasing either [bME] or [H+] will increase the average filament length.

Although tau purified from microtubule was observed to form filaments using the assembly conditions, tau purified from whole brain appeared assembly incompetent. Another study, however, was able to demonstrate the presence of 10 nm filaments in samples of whole brain tau incubated with transglutaminase, an enzyme which catalyzes intermolecular cross-links between glutamic acid and lysine residues (Dudek and Johnson, 1993). The formation of filaments morphologically similar to those shown herein, suggests that whole brain tau is capable of associating in a manner similar to that which precedes the polymerization of microtubule tau. However, in the absence of the cross-linking enzyme, it appears likely that in the case of whole brain tau, this association is reversible. This implies that differences in the post-translational modification of tau purified by these two methods can directly affect the stability of cohesive tau interactions, and that transglutaminase can induce assembly independent of these modifications.

Phosphorylation affects many of the structural and functional properties of tau. Given that normal tau was not isolated in a phosphorylation state identical to that of tau which has been incorporated into paired helical filament and straight filament, it is not surprising that these morphologies were not duplicated. Tau filaments assembled in vitro did not resemble paired helical filament, and exhibited greater flexibility than straight filament. Specific phospates which might allow for the lateral association of subunits during paired helical filament assembly, could be absent or occluded by other phosphates present in the tau purified from cycled microtubule. Likewise, the increased phosphorylation of tau incorporated into straight filament and paired helical filament could contribute to increased structural rigidity, analogous to the increase in the rigidity of tau paracrystals induced by phosphorylation (Hagestedt et al., 1989). It is likely that if the phosphorylation state of straight filament and paired helical filament could be duplicated, identical structures would form under these assembly conditions.

Using the conditions for tau polymerization defined in the present invention has several potential advantages over previously reported procedures. First, reasonable filament yields were obtained at relatively low tau concentrations (1–10 mM). Previous studies have used concentrations of 50 mM (<10 filaments/field; Montejo de Garcini and Avila, 1987) to 250 mM (Crowther et al., 1994). One study did report assembly at a tau concentration of 2.5 mM, but only in the presence of transglutaminase (Dudek and Johnson, 1993). Since this enzyme could potentially induce polymer accumulation in a manner independent of physiologically relevant post-translational modifications, this protocol might not be suitable for defining those protein modifications which result in changes in filament morphology or rates of assembly. Second, unlike conditions reported for the assembly of tau fragments (Wille et al., 1992; Crowther et al., 1992), the conditions defined herein are conducive to assembly of the full length tau protein. This is important if the contribution of all regions of the tau sequence to the assembly process are to be assessed. Third, use of these assembly conditions results in the polymerization of a morphologically homogenous population of filaments. Therefore, analyzing changes in morphology resulting from protein modification may be more straightforward than when using conditions which are reported to result in heterogenous filament populations (Montejo de Garcini et al., 1986; Wille et al., 1992; Crowther et al., 1992; Crowther et al., 1994). Finally, if chemical or enzymatic treatments of tau are to be screened for their potential ability to modulate tau polymerization in vivo, they should preferably be examined under conditions as close to physiological as possible.

A causal relation has been established between free fatty acids and the in vitro assembly of polymers related to those observed in the AD brain. Arachidonic acid was observed to stimulate the polymerization of all tau preparations examined, with assembly induced by as little as 10–20 $\mu$M free fatty acids at tau concentrations of 2.5–5 $\mu$M. In addition, measured differences in the spontaneous and inducible assembly of the different tau isolates indicates that sequence and/or phosphorylation is likely to play a role in modulating tau polymerization. The activity of kinases and phosphatases present during tissue processing and microtubule cycling is expected to produce a phosphorylation state for microtubule tau different from that of tau purified from whole brain, as has been shown for microtubule-associated protein 2. Since juvenile and adult brain contain different sets of developmentally regulated kinases and phosphatases, MTτ purified from these two sources will also differ in their phosphate content. Recombinant tau proteins are presumed to contain no phosphorylated residues. It should be stressed that none of these phosphorylation states necessarily occur in vivo. A comparison of tau assembled in the presence and absence of free fatty acids reveals a similar dependence on several physical parameters and the formation of morphologically indistinguishable filaments. Since free fatty acids appear to stimulate assembly without altering the type of filament formed, they should prove to be of general utility in studying the effects of phosphorylation and other factors that might further modulate tau polymerization.

One result that warrants closer examination due to its implications for the mechanism of tau assembly, is the reciprocal relation between filament length and filament numbers observed when the reducing potential is varied. If nucleation and elongation events compete for a limited pool of subunits, then the effects of increasing the reducing potential and thereby decreasing disulfide dependent dimerization could be interpreted in two ways. First, decreasing dimerization may promote elongation at the expense of nucleation. This implies that tau dimers formed in an excess of DTT can inhibit the addition of tau monomers to filament ends, which seems unlikely given the large excess of monomers expected to be present under these conditions. Second, decreasing dimerization may inhibit nucleation, allowing for greater elongation. Consistent with the latter interpretation is a >50% decrease in total polymer mass (filament number× average length, FIG. 13C) observed when assembly at 10 mM DTT is compared with assembly at 0.01–1.0 mM DTT, indicating that a larger reducing potential has an overall inhibitory effect on assembly. This interpretation of the data supports previous reports that intermolecular disulfide based dimerization precedes polymerization of a tau deletion construct (Wille et al., 1992; Schweers et al., 1995). A hydrophobic domain produced by folding events which precede polymerization might protect a disulfide bond shared by two apposed tau monomers, allowing for the formation of significant numbers of dimers under reducing conditions. The stimulatory effect of free fatty acids on tau polymerization could be mediated by a stabilization of this hydrophobic domain and the associated folded conformation of tau.

The ability of free fatty acids to stimulate amyloid assembly could also result from the stabilization of an assembly-competent conformation of the Aβ peptide. The thioflavin binding assay indicates that free fatty acids stimulate an increase in polymer mass, but it does not resolve the relative contributions of filament nucleation and elongation. The paucity of short filaments in the free fatty acids treated samples, however, suggests that nucleation is limited. Since spontaneous assembly is observed at 25 μM but not 10 μM peptide, in a 10 μM solution lacking free fatty acids the concentration of soluble, assembly-competent peptide might be below the critical concentration required for assembly. Stabilization of the assembly-competent conformation of the peptide by free fatty acids could drive concentrations above the critical concentration, resulting in elongation of the population of short filaments initially present in the peptide solution. Potential conformational changes are likely to be mediated by the interaction of free fatty acids with hydrophobic residues of the Aβ peptide. The reported interaction of apoE with Aβ is also dependent on hydrophobic properties of the peptide and is mediated by the lipid binding domain of apoE. Thus, the assembly promoting activity of apoE and free fatty acids may be a property shared by a variety of hydrophobic substrates. Given that β-amyloid polymerization appears to be a reversible process, any factors that increase the rate of filament elongation would decrease the net disassembly and normal clearance of amyloid polymers, thereby contributing to amyloid deposition.

Recognizing the potential contribution of free fatty acids to AD pathology, it is of interest to examine whether concentrations of free fatty acids demonstrated to stimulate polymer assembly in vitro might be of physiologic relevance in vivo. The intracellular concentration of free fatty acids has not been directly measured, but it is likely to be in the low micromolar range as inferred from the dissociation constants (0.2–3.0 μM) reported for the binding of free fatty acids to fatty acid binding proteins, a class of proteins believed to facilitate diffusion and act as intracellular buffers of free fatty acids. The induction of a free fatty acids dependent pathological effect, therefore, might be expected to occur at free fatty acids concentrations in the low micromolar range (i.e. slightly higher than normal physiologic), consistent with the apparent threshold of 5–10 μM demonstrated for the stimulation of tau assembly. In the CSF, unesterified fatty acid concentrations have also been measured in the low micromolar range ($10^{-6}$–$10^{-5}$), but are reported to rise as high as 30–50 μM in response to physical trauma. Since the concentration of albumin in the CSF is only 2–3 μM, even with 6–8 high-affinity free fatty acids binding sites the buffering capacity of albumin may be exceeded under some trauma related conditions, resulting in elevations of both extracellular, and by transmembrane diffusion, intracellular free fatty acids levels. With respect to this latter regard, there is increased amyloid deposition and an increased prevalence of AD among victims of head trauma.

The ability of unsaturated free fatty acids to stimulate tau and $A\beta_{1-40}$ assembly suggests that enzymes with phospholipase $A_2$ ($PLA_2$) activity may be relevant to the generation of AD pathology. Many $PLA_2$ enzymes are $Ca^{++}$ activated and coupled directly or indirectly to signal transducing, heterotrimeric G proteins, which are in turn activated by many factors, including receptor bound neurotransmitters, hormones, and cytokines, bacterial toxins, and aluminum fluorate. Levels of arachidonic acid produced by $PLA_2$ activity are elevated during long term potentiation (LTP), a phenomenon associated with the process of memory formation. Under some conditions, lecithin:cholesterol acyltransferase (LCAT) also exhibits a $PLA_2$ activity. Serum LCAT normally liberates fatty acids from phospholipids and catalyzes their esterification with free cholesterol: in the absence of sufficient free cholesterol the net effect is the generation of free fatty acids. This enzyme, which is synthesized in the brain and is a component of lipoproteins in the CSF, may be of particular importance given that it is activated by apoE, a recently identified genetic risk factor for AD. It is not known whether the risk-defining allelic variations in apoE can modulate its activation of LCAT.

Figure 16:
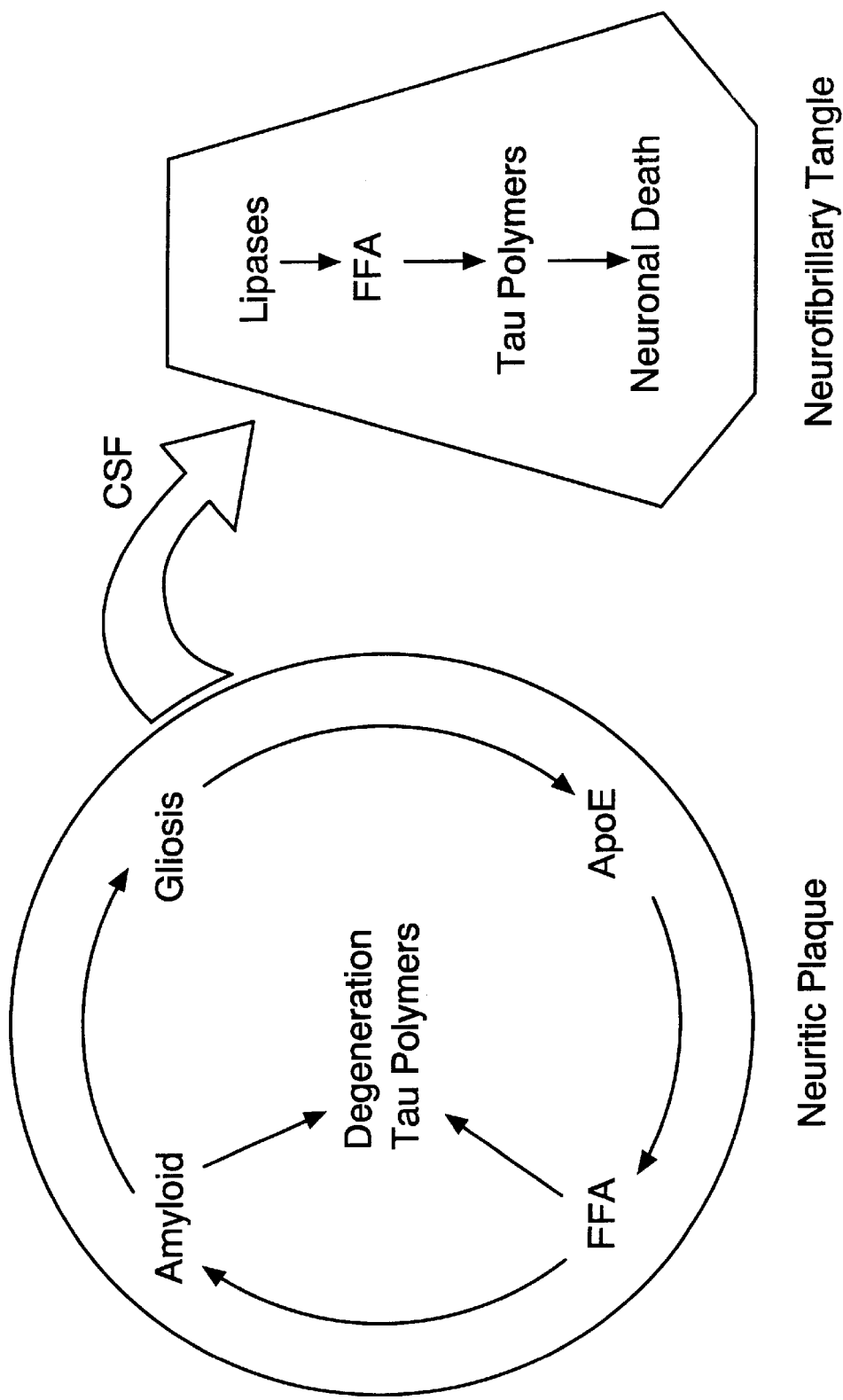
FIG. 16 shows the free fatty acids model of AD pathogenesis. The relationship between the various elements postulated to contribute to the formation of NP and NFT are shown, for the case in which apoE is a risk defining factor. The common effector molecule is the free fatty acids, which can be carried from its point of origin in the NP to anatomically distant sites of NFT formation by the circulating CSF.
Figure 17:
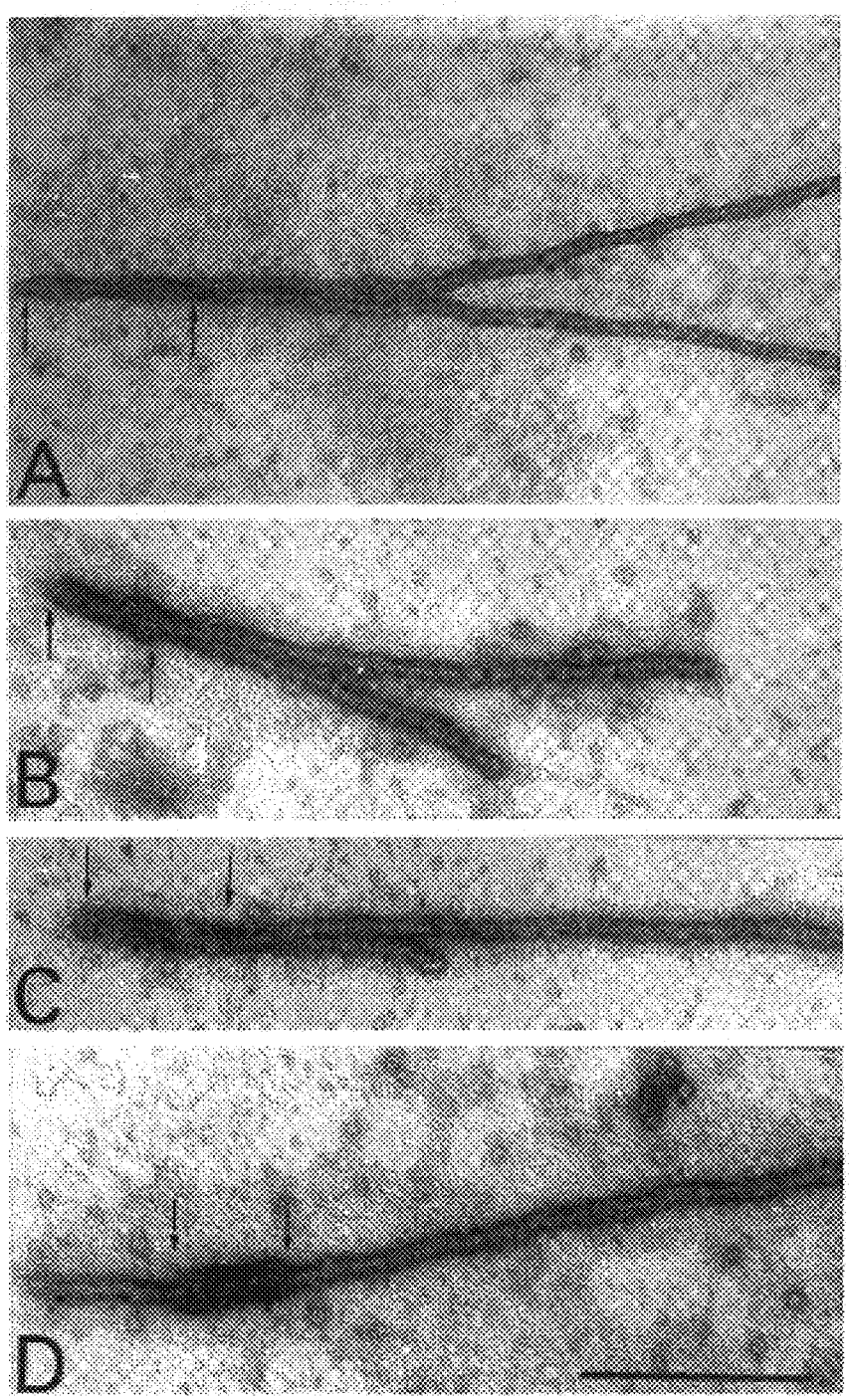
FIG. 17 shows that paired helical filaments, provided by Dr. Sharon Greenberg, were purified by the method of Greenberg and Davies (no SDS extraction) and resuspended in buffer A. P11 rat microtubule tau (400 µg/ml), PHF (250 µg/ml), and buffer B (borate saline, 20 mM DTT) were mixed at a ratio of 1:1:2, and incubated 2–3 days at 37° C. in the presence of 50 µM arachidonic acid. The resulting hybrid morphologies are interpreted as two straight filaments emanating from the same end of a PHF (FIGS. 17A–C) or a single straight filament emanating from both ends of a PHF (FIG. 17D). Bar=100 nm.

In a multifactorial disease characterized by the appearance of two distinct lesions that occur concomitantly but are nonetheless distributed through the brain in a non-correlative manner, the diffusable free fatty acids are attractive candidates as effectors of pathogenesis. The following model (schematized in FIG. 16) is proposed as an example of how the spatial and temporal progression of AD could result from free fatty acids dysequilibria. Beginning with the earliest stage of NP formation, a toxic effect produced by an initial deposition of filamentous amyloid results in the degeneration of neurites and the activation of glial cells in the surrounding neuropil. This initial polymerization of amyloid occurs when the local concentration of Ab surpasses the critical concentration for assembly: this might result from an increase in peptide concentration or a decrease in the critical concentration, either of which could be attributed to a number of factors of genetic or environmental origin. As astrocytes associated with the primordial plaque are activated, they exhibit an increase in apoE production, as is in fact observed in the AD brain. The different isoforms of apoE, by virtue of their role in the regulation of lipid trafficking and metabolism, are able to effect an isoform dependent increase in free fatty acids release. This might be envisioned as occurring in a number of ways, invoking only elements of previously defined metabolic pathways. With the apoE dependent stimulation of free fatty acids release comes a further induction of amyloid assembly, and the establishment of a positive feedback loop that accelerates the further evolution of the plaque. In addition, local increases in free fatty acids would induce the assembly of tau polymers within degenerating neurites associated with the plaque. With regards to tau polymerization in NFT and neuropil threads, it should first be noted that tau proteins are constituitively exposed to some baseline concentration of free fatty acids as a result of the normal activity of intracellular lipases. Neurons could be primed for the assembly of tau filaments by any number of conditions that conspire to increase this baseline level of exposure. If intracellular levels of free fatty acids are supplemented to a sufficient degree by NP derived free fatty acids circulating in the CSF, then the process of tau polymerization would be initiated within the population of primed neurons.

Since lipid metabolism in the brain is at present poorly understood, the means by which increased levels of apoe could potentially modulate free fatty acids release must in large part be discussed in light of the known roles of this protein in serum lipid metabolism. As mentioned above, apoE is an activator of LCAT. If the rate of cholesterol esterification by LCAT is limited by the availability of unesterified cholesterol in the CSF, then an increased activation of LCAT might cause the deacylating activity of the enzyme to exceed the cholesterol esterifying activity of the enzyme, resulting in an extracellular release of free fatty acids from apoE-associated lipids. Alternatively, apoE might modulate intracellular release of free fatty acids through its presentation of lipids to cells. In this regard, an isoform specific binding of apoE to lipoproteins and the LDL receptor has been demonstrated. Another apoE receptor, the very low density lipoprotein receptor, is present at increased levels in the AD brain and has been identified as a risk factor for AD in a Japanese population: A two-fold increase in the incidence of AD was observed among individuals who were homozygous for a specific allele of this receptor.

In the free fatty acids model of pathogenesis, the relevant initiating event is the assembly of amyloid filaments, consistent with the amyloid cascade hypothesis. In contrast to this hypothesis, however, risk factors for AD would not be limited to those that increase rates of amyloid polymerization, but would also include factors that link NP genesis to mechanisms of free fatty acids release. The free fatty acids model also implies that the targeting of a neuron for NFT formation is separable from the subsequent death of that neuron, and that tau polymerization contributes directly to neuronal dysfunction and the resulting clinical manifestations of the disease. This contrasts with the view that NFT are merely "tombstones" of the necrotic process. Since free fatty acids derived from sources other than NP could also potentially induce tau polymerization, NFT might be expected to occur in other pathological states characterized by intracellular free fatty acids release and the absence of NP. Similarly, in the absence of risk factors that link the deposition of amyloid to free fatty acids release, the assembly of amyloid filaments could occur without a concomitant induction of tau pathology. As noted, factors that contribute to the initial deposition of amyloid and the priming of neurons for NFT formation are probably numerous and of varied origin, allowing for the considerable variation in the relative number of NFT and NP that are encountered in AD case comparisons.

The demonstration of free fatty acids stimulated tau and amyloid assembly provides new evidence that formation of these structurally unique lesions in AD could be mediated by a common effector molecule. The relevance of free fatty acids to biological systems leads to a straightforward model of pathogenesis that effectively incorporates identified risk factors and much of the observed pathology. The free fatty acids model of pathogenesis predicts that CSF levels of free fatty acids are increased in AD, and that these levels would be proportional to the total plaque load in the brain. This model also suggests an explanation for the concomitant appearance of the extracellular amyloid and intracellular tau polymers that is uniquely observed in the AD brain. The implication of various enzymes with lipase activity in AD pathogenesis suggests potential therapeutic targets for the treatment of Alzheimer's disease.

References cited herein include:

Aebi, et al., 1988. Unifying principles in intermediate filament (IF) structure and assembly. Protoplasma. 145: 73–81.

Berkowitz, et al.,. 1977. Separation and characterization of microtubule proteins from calf brain. Biochemistry. 16: 5610–5617.

Braak, et al., 1986. Occurrence of neuropil threads in the senile human brain and in Alzheimer's disease: a third location of paired helical filaments outside of neurofibrillary tangles and neuritic plaques. Neurosci. Lett. 65: 351–355.

Bugiani, et al.,1979 The structure of subcortical neurofibrillary tangles in progressive supranuclear palsy. Acta Neuropath. 45: 147–152.

Burns, R. G. 1991. Assembly of chick brain MAP2-tubulin microtubule protein. Biochem. J. 277: 231–238.

Cleveland, et al., 1977a. Purification of tau, a microtubule-associated protein that induces assembly of microtubules from purified tubulin. J. Mol. Biol. 116: 207–225.

Cleveland, et al., 1977b. Physical and chemical properties of purified tau factor and the role of tau in microtubule assembly. J. Mol. Biol. 116: 227–247.

Crowther, R. A.. 1991. Straight and paired helical filaments in Alzheimer disease have a common structural unit. Proc. Natl. Acad. Sci. USA. 88: 2288–2292.

Crowther, et al., 1992. The microtubule binding repeats of tau protein assemble into filaments like those found in Alzheimer's disease. FEBS Lett. 309: 199–202.

Crowther, et al.,1994. Assembly of Alzheimer-like filaments from full-length tau protein. FEBS Lett. 337: 135–138.

Dudek, et al., 1993. Transglutaminase catalyzes the formation of sodium dodecyl sulfate-insoluble, Alz-50-reactive polymers of t. J. Neurochem. 61: 1159–1162.

Geisler, et al., 1981. Self-assembly in vitro of the 68,000 molecular weight component of the mammalian neurofilament triplet proteins into intermediate-sized filaments. J. Mol. Biol. 151: 565–571.

Greenberg, et al., 1990. A preparation of Alzheimer paired helical filaments that displays distinct t proteins by polyacrylamide gel electrophoresis. Proc. Natl. Acad. Sci. USA 87: 5827–5831.

Grundke-Iqbal, et al., 1986. Microtubule-associated protein tau: a component of Alzheimer paired helical filaments. J. Biol. Chem. 261: 6084–6089.

Hagestedt, et al., 1989. Tau protein becomes long and stiff upon phosphorylation: correlation between paracrystalline structure and degree of phosphorylation. J. Cell Biol. 109: 1643–1651.

Hasegawa, et al.,1992. Protein sequence and mass spectrometric analyses of tau in the Alzheimer's disease brain. J. Biol. Chem. 267: 17047–17054.

Hirano et al.,1968. The fine structure of some intraganglionic alterations: Neurofibrillary tangles, granulovacuolar bodies and "rod-like" structures as seen in Guam amyotrophic lateral sclerosis and Parkinsonism-dementia complex. J. Neuropath. Exp. Neurol. 27: 167–182.

Hirokawa, et al.,1988. Tau proteins: the molecular structure and mode of binding on microtubules. J. Cell Biol. 107: 1449–1459.

Hisanaoa, et al.,1988. Structure of the peripheral domains of neurofilaments revealed by low angle rotary shadowing. J. Mol. Biol. 202: 297–305.

Hwang, et al.,1992. Oxidized redox state of glutathione in the endoplasmic reticulum. Science. 257: 1496–1502.

Iqbal, et al.,1984. Alzheimer paired helical filaments: bulk isolation, solubility, and protein composition. Acta Neuropathol. 62: 167–177.

Johnson, et al., 1989. Proteolysis of tau by calpain. Biochem. Biophys. Res. Comm. 163: 1505–1511.

Kidd, M. 1963. Paired helical filaments in electron microscopy of Alzheimer's disease. Nature. 197: 192–193.

Kondo, et al.,1988. The carboxyl third of tau is tightly bound to paired helical filaments. Neuron. 1: 827–834.

Kosik, et al., 1986. Microtubule-associated protein tau (t) is a major antigenic component of paired helical filaments in Alzheimer disease. Proc. Natl. Acad. Sci. USA. 83: 4044–4048.

Kowall,et al.,1987. Axonal disruption and aberrant localization of tau protein characterize the neuropil pathology of Alzheimer's disease. Ann. Neurol. 22: 639–643.

Ksiezak-Reding, et al., 1992. Phospate analysis and dephosphorylation of modified tau associated with paired helical filaments. Brain Res. 597: 209–219.

Laemmli, U. K. 1970. Cleavage of structural proteins during the assembly of the head of bacteriophage T4. Nature. 227: 680–685.

Lee, G. 1990. Tau protein: an update on structure and function. Cell Motil. Cytoskeleton. 15: 199–203.

Lee, et al.,1991. A68: A major subunit of paired helical filaments and derivatized forms of normal tau. Science 251: 675–678.

Lindwall, G., and R. D. Cole. 1984. The purification of tau protein and the occurrence of two phosphorylation states of tau in brain. J. Biol. Chem. 259: 12241–12245.

Lowry, et al.,1951. Protein measurements with the Folin phenol reagent. J. Biol. Chem. 193: 265–275.

McKee, et al., 1991. Neuritic pathology and dementia in Alzheimer's disease. Ann. Neurol. 30: 156–165.

Metuzals, et al.,1981. Cell Tissue Res. 214: 455–482.

Montejo et al.,1986. Self assembly of microtubule associated protein tau into filaments resembling those found in Alzheimer disease. Biochem. Biophys. Res. Comm. 141: 790–796.

Montejo de Garcini, E., and J. Avila. 1987. In vitro conditions for the self-polymerization of the microtubule-associated protein, tau factor. J. Biochem. 102: 1415–1421.

Papasozpmenos, et al., 1987. Phosphorylation determines two distinct species of tau in the central nervous system. Cell Motil. Cytoskel. 8: 210–226.

Papasozomenos, S. Ch. 1989. Tau protein immunoreactivity in dementia of the Alzheimer type: II. Electron microscopy and pathogenetic implications. Lab. Invest. 60: 375–388.

Perry, et al.,1987. Immunocytochemical properties of Alzheimer straight filaments. J. Neurosci. 7: 3736–3738.

Probst, et al.,1989. Senile plaque neurites fail to demonstrate anti-microtubule-associated protein-tau immunoreactive proteins in the absence of neurofibrillary tangles in the neocortex. Acta Neuropathol. 77: 430–436.

Ruben, et al., 1991. The microtubule-associated protein tau forms a triple-stranded left-hand helical polymer. J. Biol. Chem. 266: 22019–22027.

Ruben, et al.,1993. The organization of the microtubule associated protein tau in Alzheimer paired helical filaments. Brain Res. 602: 1–13.

Sandoval, I. V., and K. Weber. 1980. Different tubulin polymers are produced by microtubule-associated proteins MAP2 and t in the presence of guanosine 5'-(a,b-methylene) triphosphate. J. Biol. Chem. 255: 8952–8954.

Shelanski, et al.,1973. Microtubule assembly in the absence of added nucleotide. Proc. Natl. Acad. Sci. USA. 70: 765–768.

Sloboda, et al., 1976. Microtubule-associated proteins and the stimulation of tubulin assembly in vitro. Biochemistry. 15: 4497–4505.

Symmons, et al.,1991. Assembly of chick brain MAP2-tubulin microtubule protein. *Biochem. J.* 277: 245–253.

Tellez-Nagel, et al.,1973. Ultrastructure of neurofibrillary tangles in Steele-Richardson-Olszewski syndrome. *Arch. Neurol.* 29: 324–327.

Towbin, et al.,1979. Electrophoretic transfer of proteins from polyacrylamide gels to nitrocellulose sheets: Procedure and some applications. *Proc. Natl. Acad. Sci. USA*. 76: 4350–4354.

Tsuyama, et al.,1986. Calcium/phospholipid-dependent kinase recognizes sites in microtubule-associated protein 2 which are phosphorylated in living brain and are not accessible to other kinases. *J. Biol. Chem.* 261: 4110–4116.

Vallee, R. B. 1982. A taxol-dependent procedure for the isolation of microtubules and microtubule-associated proteins (MAPs). J. Cell Biol. 92: 435–442.

Weingarten, et al.,. 1975. A protein factor essential for microtubule assembly. *Proc. Natl. Acad. Sci. USA*. 72: 1858–1862.

Wille, et al.,1992. Alzheimer-like paired helical filaments and antiparallel dimers formed from microtubule-associated protein tau in vitro. J. Cell Biol. 118: 573–584.

Wishik, et al., 1985. Subunit structure of paired helical filaments in Alzheimer's disease. *J. Cell Biol.* 100: 1905–1912.

Wischik, et al.,1988. Isolation of a fragment of tau derived from the core of the paired helical filament of Alzheimer disease. *Proc. Natl. Acad. Sci. USA*. 85: 4506–4510.

Wisniewski, et al.,1984. Ultrastructure of paired helical filaments of Alzheimer's neurofibrillary tangles. *J. Neuropath. Exp. Neurol.* 43: 643–656.

Wisniewski, et al.,1979. Alzheimer neurofibrillary tangles in diseases other than senile and presenile dementia. *Ann. Neurol.* 5: 288–294.

Wisniewski, et al.,. 1985. Occurence of neuropathological changes and dementia of Alzheimer's disease in Down's syndrome. *Ann. Neurol.* 17: 278–282.

Yagishita, et al.,1981. Reappraisal to the fine structure of Alzheimer's neurofibrillary tangles. *Acta Neuropathol.* 54: 239–246.

Yamaguchi, et al., 1990. Ultrastructure of the neuropil threads in the Alzheimer brain: their dendritic origin and accumulation in the senile plaques. *Acta Neuropathol.* 80: 368–374.

Burgoyne and Morgan, 1990. The control of free arachidonic acid levels. *TINS.* 15: 365–366.

Cistola et al., 1988. Ionization and phase behavior of fatty acids in water: application of the Gibbs phase rule. *Biochemistry.* 27: 1881–1888.

Clements et al., 1991. Increase in arachidonic acid concentration in a postsynaptic membrane fraction following the induction of long-terin potentiation in the dentate gyrus. *Neuroscience,* 45(2): 379–389.

Fernandez et al., 1988., *Neurol. Res.* 10(2): 66–68.

Naor et al., 1988., *Mol. Endocrin.* 2(11): 1043–1048.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of regulating the assembly of the protein tau in the brain of a mammal in need of such treatment comprising the step of administering to said mammal a pharmacologically effective amount of an inhibitor of fatty acid liberation or release, wherein the inhibitor of fatty acid liberation or release is a terpene selected from the group consisting of menthol, menthone, and camphor.

2. The method of claim 1, wherein said terpene is administered in an amount from about 0.2 mg/kg per day to about 20 mg/kg per day.

3. A method of regulating the assembly of the protein tau in a brain of a mammal in need of such regulation, said method comprising administering to the mammal a pharmacologically effective amount of an inhibitor of fatty acid liberation or release, wherein the inhibitor is L-propranolol, D-propranolol, or mixtures thereof and wherein the inhibitor is administered in an amount from about 2.5 mg per day to less than 10 mg per day.

4. A method as defined in claim 3 wherein the mammal is a human.

5. A method as defined in claim 1, wherein the mammal is a human.

* * * * *